(12) United States Patent
Miller et al.

(10) Patent No.: US 7,824,390 B2
(45) Date of Patent: Nov. 2, 2010

(54) SPINAL DIAGNOSTIC METHODS AND APPARATUS

(75) Inventors: David R. Miller, Palo Alto, CA (US); Todd Alamin, Woodside, CA (US); Peter F. Campbell, San Jose, CA (US)

(73) Assignee: Kyphon SÀRL, Neuchâtel (CH)

( * ) Notice: Subject to any disclaimer, the term of this patent is extended or adjusted under 35 U.S.C. 154(b) by 600 days.

(21) Appl. No.: 11/616,213

(22) Filed: Dec. 26, 2006

(65) Prior Publication Data
US 2008/0215033 A1 Sep. 4, 2008

Related U.S. Application Data

(63) Continuation-in-part of application No. 10/825,961, filed on Apr. 16, 2004, now Pat. No. 7,452,351, and a continuation of application No. 11/597,349, filed as application No. PCT/US2005/012981 on Apr. 15, 2005.

(51) Int. Cl.
*A61M 31/00* (2006.01)
(52) U.S. Cl. .................. 604/509; 604/104; 604/164.01
(58) Field of Classification Search ................ 46/96.01, 46/506, 509, 510
See application file for complete search history.

(56) References Cited

U.S. PATENT DOCUMENTS

| | | | |
|---|---|---|---|
| 2,498,672 A * | 2/1950 | Glass | .......................... 604/155 |
| 3,190,291 A | 6/1965 | Foley | |
| 3,482,576 A | 12/1969 | Ericson | |
| 3,885,561 A | 5/1975 | Cami | |
| 3,952,742 A | 4/1976 | Taylor | |
| 4,419,095 A | 12/1983 | Nebergall et al. | |
| 4,419,819 A | 12/1983 | Dickhudt | |
| 4,543,087 A | 9/1985 | Sommercorn et al. | |
| 4,573,448 A | 3/1986 | Kambin | |

(Continued)

FOREIGN PATENT DOCUMENTS

DE 4028487 9/1990

(Continued)

OTHER PUBLICATIONS

Bogduk et al. *Spine care: Discography* Chapter 14, pp. 219-238, 2 v. :ill. St. Louis : Mosby, c1995.; 29 cm.

(Continued)

*Primary Examiner*—Nicholas D Lucchesi
*Assistant Examiner*—Laura A Bouchelle
(74) *Attorney, Agent, or Firm*—Haynes and Boone, LLP

(57) ABSTRACT

Methods, devices and systems facilitate diagnosis, and in some cases treatment, of back pain originating in intervertebral discs. Methods generally involve introducing one or more substances into one or more discs using a catheter device. In one embodiment, a patient assumes a position that causes back pain, and a substance such as an anesthetic or analgesic is introduced into the disc to determine whether the substance relieves the pain. Injections into multiple discs may optionally be performed, to help pinpoint a disc as a source of the patient's pain. In some embodiments, the catheter device is left in place, and possibly coupled with another implantable device, to provide treatment of one or more discs. A catheter device includes at least one anchoring member for maintaining a distal portion of the catheter within a disc.

11 Claims, 26 Drawing Sheets

U.S. PATENT DOCUMENTS

| | | | |
|---|---|---|---|
| 4,626,241 A | 12/1986 | Campbell et al. | |
| 4,684,363 A | 8/1987 | Ari et al. | |
| 4,715,378 A | 12/1987 | Pope | |
| 4,737,146 A | 4/1988 | Amaki et al. | |
| 4,782,834 A | 11/1988 | Maguire et al. | |
| 4,904,260 A | 2/1990 | Ray et al. | |
| 4,919,651 A | 4/1990 | Doane | |
| 4,964,853 A | 10/1990 | Sugiyama et al. | |
| 4,968,298 A | 11/1990 | Michelson | |
| 4,973,305 A * | 11/1990 | Goltzer | 604/509 |
| 4,994,032 A | 2/1991 | Sugiyama et al. | |
| 4,994,036 A | 2/1991 | Biscoping et al. | |
| 5,004,456 A | 4/1991 | Botterbusch et al. | |
| 5,024,655 A | 6/1991 | Freeman et al. | |
| 5,024,659 A | 6/1991 | Sjostrom | |
| 5,084,016 A | 1/1992 | Freeman et al. | |
| 5,129,889 A | 7/1992 | Hahn et al. | |
| 5,163,989 A | 11/1992 | Campbell et al. | |
| 5,215,105 A | 6/1993 | Kizelshteyn et al. | |
| 5,232,442 A | 8/1993 | Johnson et al. | |
| 5,234,406 A | 8/1993 | Drasner et al. | |
| 5,250,069 A | 10/1993 | Nobuyoshi et al. | |
| 5,267,960 A | 12/1993 | Hayman et al. | |
| 5,344,399 A | 9/1994 | DeVries | |
| 5,344,439 A | 9/1994 | Otten | |
| 5,354,282 A | 10/1994 | Bierman | |
| 5,395,317 A | 3/1995 | Kambin | |
| 5,405,334 A | 4/1995 | Roth et al. | |
| 5,409,483 A | 4/1995 | Campbell et al. | |
| 5,433,739 A * | 7/1995 | Sluijter et al. | 607/99 |
| 5,533,986 A | 7/1996 | Mottola et al. | |
| 5,571,147 A | 11/1996 | Sluijter et al. | |
| 5,591,132 A | 1/1997 | Carrie | |
| 5,647,860 A | 7/1997 | Roth et al. | |
| 5,665,076 A | 9/1997 | Roth et al. | |
| 5,693,032 A | 12/1997 | Bierman | |
| 5,762,629 A | 6/1998 | Kambin | |
| 5,772,639 A | 6/1998 | Lampropoulos et al. | |
| 5,800,402 A | 9/1998 | Bierman | |
| 5,800,407 A | 9/1998 | Eldor | |
| 5,833,666 A | 11/1998 | Davis | |
| 5,833,667 A | 11/1998 | Bierman | |
| 5,865,802 A | 2/1999 | Yoon et al. | |
| 5,908,405 A | 6/1999 | Imran | |
| 5,954,635 A | 9/1999 | Foley et al. | |
| 5,980,504 A | 11/1999 | Sharkey et al. | |
| 6,033,438 A | 3/2000 | Bianchi et al. | |
| 6,054,429 A | 4/2000 | Bowersox et al. | |
| 6,080,160 A | 6/2000 | Chen et al. | |
| 6,086,589 A | 7/2000 | Kuslich et al. | |
| 6,095,149 A | 8/2000 | Sharkey et al. | |
| 6,146,401 A | 11/2000 | Yoon et al. | |
| 6,187,000 B1 | 2/2001 | Davison et al. | |
| 6,190,370 B1 | 2/2001 | Tsui | |
| 6,224,630 B1 | 5/2001 | Bao et al. | |
| 6,248,110 B1 | 6/2001 | Reiley et al. | |
| 6,258,086 B1 | 7/2001 | Ashley et al. | |
| 6,261,311 B1 | 7/2001 | Sharkey et al. | |
| 6,368,315 B1 | 4/2002 | Gillis et al. | |
| 6,387,076 B1 | 5/2002 | Landuyt | |
| 6,423,083 B2 | 7/2002 | Reiley et al. | |
| 6,443,988 B2 | 9/2002 | Felt et al. | |
| 6,524,320 B2 | 2/2003 | DiPoto | |
| 6,544,215 B1 | 4/2003 | Bencini et al. | |
| 6,547,810 B1 | 4/2003 | Sharkey et al. | |
| 6,554,802 B1 | 4/2003 | Pearson et al. | |
| 6,558,390 B2 | 5/2003 | Cragg | |
| 6,562,033 B2 | 5/2003 | Shah et al. | |
| 6,575,979 B1 | 6/2003 | Cragg | |
| 6,602,248 B1 | 8/2003 | Sharps et al. | |
| 6,613,044 B2 | 9/2003 | Carl | |
| 6,613,054 B2 * | 9/2003 | Scribner et al. | 606/93 |
| 6,638,276 B2 | 10/2003 | Sharkey et al. | |
| 6,648,873 B2 | 11/2003 | Arenberg | |
| 6,652,553 B2 | 11/2003 | Davison et al. | |
| 6,673,063 B2 | 1/2004 | Brett | |
| 6,676,643 B2 | 1/2004 | Brushey | |
| 6,685,695 B2 | 2/2004 | Ferree | |
| 6,706,069 B2 | 3/2004 | Berger | |
| 6,733,496 B2 | 5/2004 | Sharkey et al. | |
| 6,733,534 B2 | 5/2004 | Sherman | |
| 6,736,815 B2 | 5/2004 | Ginn | |
| 6,736,835 B2 | 5/2004 | Pellegrino et al. | |
| 6,800,084 B2 | 10/2004 | Davison et al. | |
| 6,805,715 B2 * | 10/2004 | Reuter et al. | 623/17.12 |
| 6,811,558 B2 | 11/2004 | Davison et al. | |
| 6,812,211 B2 | 11/2004 | Slivka et al. | |
| 6,821,276 B2 | 11/2004 | Lambrecht et al. | |
| 6,827,716 B2 | 12/2004 | Ryan et al. | |
| 6,835,205 B2 | 12/2004 | Atkinson et al. | |
| 6,837,891 B2 | 1/2005 | Davison et al. | |
| 6,852,095 B1 | 2/2005 | Ray | |
| 6,878,155 B2 | 4/2005 | Sharkey et al. | |
| 6,899,713 B2 | 5/2005 | Shaolian et al. | |
| 6,899,716 B2 | 5/2005 | Cragg | |
| 6,921,403 B2 | 7/2005 | Cragg et al. | |
| 7,069,087 B2 | 6/2006 | Sharkey et al. | |
| 7,108,677 B2 | 9/2006 | Courtney et al. | |
| 2001/0049518 A1 | 12/2001 | Hoch | |
| 2002/0052576 A1 | 5/2002 | Massengale | |
| 2002/0120259 A1 | 8/2002 | Lettice et al. | |
| 2002/0151885 A1 | 10/2002 | Underwood et al. | |
| 2002/0156530 A1 | 10/2002 | Lambrecht et al. | |
| 2002/0173796 A1 | 11/2002 | Cragg | |
| 2003/0032963 A1 | 2/2003 | Reiss et al. | |
| 2003/0040796 A1 | 2/2003 | Ferree | |
| 2003/0055454 A1 | 3/2003 | Zucker | |
| 2003/0083642 A1 | 5/2003 | Boyd et al. | |
| 2003/0135156 A1 | 7/2003 | Bencini et al. | |
| 2003/0171744 A1 | 9/2003 | Leung et al. | |
| 2003/0208206 A1 | 11/2003 | Gitis et al. | |
| 2003/0216721 A1 | 11/2003 | Diederich et al. | |
| 2003/0216748 A1 | 11/2003 | Gitis et al. | |
| 2003/0216768 A1 | 11/2003 | Gitis et al. | |
| 2003/0229372 A1 | 12/2003 | Reiley et al. | |
| 2004/0019381 A1 | 1/2004 | Pflueger | |
| 2004/0024399 A1 | 2/2004 | Sharps et al. | |
| 2004/0024410 A1 | 2/2004 | Olson et al. | |
| 2004/0054414 A1 | 3/2004 | Trieu et al. | |
| 2004/0083002 A1 | 4/2004 | Belef et al. | |
| 2004/0092948 A1 | 5/2004 | Stevens et al. | |
| 2004/0116977 A1 | 6/2004 | Finch et al. | |
| 2004/0133276 A1 | 7/2004 | Lang et al. | |
| 2004/0138525 A1 | 7/2004 | Saadat et al. | |
| 2004/0138754 A1 | 7/2004 | Lang et al. | |
| 2004/0181178 A1 | 9/2004 | Aldrich et al. | |
| 2004/0186471 A1 | 9/2004 | Trieu | |
| 2004/0193274 A1 | 9/2004 | Trieu | |
| 2004/0215193 A1 | 10/2004 | Shaolian et al. | |
| 2004/0220545 A1 | 11/2004 | Heruth et al. | |
| 2004/0220546 A1 | 11/2004 | Heruth et al. | |
| 2004/0220547 A1 | 11/2004 | Heruth et al. | |
| 2005/0059930 A1 | 3/2005 | Garrison et al. | |
| 2005/0059931 A1 | 3/2005 | Garrison et al. | |
| 2005/0065397 A1 | 3/2005 | Saadat et al. | |
| 2005/0065401 A1 | 3/2005 | Saadat et al. | |
| 2005/0070913 A1 | 3/2005 | Milbocker et al. | |
| 2005/0085790 A1 | 4/2005 | Guest et al. | |
| 2005/0107663 A1 | 5/2005 | Saadat et al. | |
| 2005/0113640 A1 | 5/2005 | Saadat et al. | |
| 2005/0118228 A1 | 6/2005 | Trieu | |
| 2005/0119754 A1 | 6/2005 | Trieu et al. | |
| 2005/0203501 A1 | 9/2005 | Aldrich et al. | |
| 2005/0245938 A1 | 11/2005 | Kochan | |

2005/0246023 A1   11/2005   Yeung

FOREIGN PATENT DOCUMENTS

| EP | 0 931 560 A1 | 7/1999 |
|---|---|---|
| WO | WO 99/64869 A2 | 12/1999 |
| WO | WO 03/012506 A2 | 3/2003 |
| WO | WO 03/049669 A2 | 6/2003 |

OTHER PUBLICATIONS

Caragee, "Provocative discography in patients after limited lumbar discetomy: A controlled, randomized study of pain response in symptomatic and asymptomatic subjects," *Spine* 2000; 25:3065-71.

Caragee, "Is Lumbar Disography a Determinate of Discogenic Low Back Pain: Provocative Discography Reconsidered," *Corr. Rev. Pain* 2000: 4(4):301-8.

Colhoun et al., "Prococative Discography as a Guide to planning Operations on the Spine," *J Bone Joint Surg Br* 1988; 70:267-71.

Finch et al., "Analgesic Discography and Magnetic Resonance Imaging (MRI)" *Pain*, (1990) Supp 5: S285 [Abstract Only].

Fraser, "Chymopapain for the Treatment of Intervertebral Disc Herniation. The Final Report of a Double Blind Study," *Spine*, (Nov.-Dec. 1987), 9(8):815-818. [Abstract Only].

Gebhard et al., "Percutaneous Discectomy for the Treatment of Bacterial Discitis," *Spine*, (1994) 19(7):855-857.

Gill et al. "Functional Results After Anterior Lumbar Fusion at L5/S1 in Patients with Normal and Abnormal MRI Scans," *Spine* 1992:17:940-2.

Hadjipavlou et al., "Percutaneous Transpedicular Discectomy and Drainage in Pyogenic Spondylodiscitis," *Am J of Orthopedics*, (Mar. 1998), pp. 188-197.

Hadjipavlou et al., "Percutaneous Transpedicular Discectomy and Drainage in Pyogenic Spondylodiscitis," *Eur Spine J* (2004), 13:707-713.

Jeanneret et al., "Treatment of Osteomyelitis of the Spine Using Percutaneous Suction/Irrigation and Percutaneous Exsternal Spinal Fixation," *J of Spinal Disorders*, 7(3):185-205.

Kotilanen et al, "Intradiscal Glycerol or Bupivacaine in the Treatment of Low Back Pain", *Acta Neurochir (Wien)*, (1997) 139 (6):541-545. [Abstract Only].

Maroon et al., "Percutaneous Automated Discetomy: A New Method for Lumber Disc Removal," *J Neurosurg* (1987), 66:143-146.

Minamide et al., "Effects of Basic Fibroblast Growth Factor on Spontaneous Resorption of Herniated Intervertebral Discs. An Experimental Study in the Rabbit," *Spine*, (May 15, 1999), 24 (10):940-945. [Abstract Only].

Nishimura et al., "Percutaneous Reinsertion of the Nucleus Pulposus. An Experimental Study," *Spine*, (Jul. 15, 1998), 23(14):1531-1538, discussion 1539.

Okuma et al., "Reinsertion of Stimulated Nucleus Pulposus Cells Retards Intervertebral Disc Degeneration: An In Vitro and In Vivo Experimental Study," *J Orthop Res*, Nov. 2000; 18(6):988-997 [Abstract Only].

Osler, "Cervical Analgesic Discography. A Test for Diagnosis of the Painful Disc Syndrome," *S Afr Med J.*, (Mar. 21, 1987), 71(6):363 [Abstract Only].

Osti et al., "Discitis After Discography. The Role of Prophylactic Antibiotics", *J Bone Joint Surg Br.* (Mar. 1990), 72(2):271-274. [Abstract Only].

Roth, "Cervical Analgesic Discography. A New Test for the definitive Diagnosis of the Painful Disk Syndrome," *JAMA*, ( Apr. 19, 1976), 235(16):1713-1714. [Abstract Only].

Takahashi et al., "Experimental Study on Chemonucleolysis. With Special Reference to Change of Intrasical Pressure," *Spine*, (Jul.-Aug. 1986), 11(6)617-620. [Abstract Only].

Watters et al., "Percutaneous Diskectomy for Disk Space Infections," *J of Southern Orthopaedic Association*, (Winter 1994), 3(4): 283-289.

Wetzei et al. "The Treatment of Lumbar Spinal Pain Syndromes Diagnosed by Discography. Lumbar Arthrodesis," *Spine* 1994:19:792-800.

Wilkinson et al., "Intradiscal Corticosteroids in the Treatment of Lumbar and Cervical Disc Problems," *Spine*, (Jul. —Aug. 1980), 5(4):385-389 [Abstract Only], 1 Page.

Wittenberg et al., "Five-Year Results From Chemounucleoysis with Chymopapain or Collagenase: A Prospective Randomized Study," *Spine*, (Sep. 1, 2001), 26(17):1835-1841 [Abstract Only], 1 Page.

* cited by examiner

SPINAL DIAGNOSTIC METHODS AND APPARATUS

CROSS-REFERENCES TO RELATED APPLICATIONS

This application is a Continuation-in-Part of application Ser. No. 10/825,961 filed on Apr. 16, 2004, and is a continuation of U.S. application Ser. No. 11/597,349, which claims priority under 35 USC 371 from PCT/US2005/012981 filed on Apr. 15, 2005, the full disclosures of which are incorporated herein by reference.

BACKGROUND OF THE INVENTION

Field of the Invention

The present invention generally relates to medical devices and methods. More particularly, the present invention relates to devices and methods for diagnosing and/or treating spinal pain Back pain takes an enormous toll on the health and productivity of people around the world. According to the American Academy of Orthopedic Surgeons, approximately 80 percent of Americans will experience back pain at some time in their life. In just the year 2000, approximately 26 million visits were made to physicians' offices due to back problems in the United States. On any one day, it is estimated that 5% of the working population in America is disabled by back pain.

Unfortunately, back pain is not only extremely common, but can also be difficult to accurately diagnose and effectively treat. Challenges stem from the fact that it is often difficult to pinpoint exactly what is causing a patient's pain or even where the pain originates. Although a number of effective treatments exist for various types of back pain, a number of them are highly invasive and may actually exacerbate pain or cause pain in other parts of the back. Therefore, due to the challenges involved in diagnosing and treating back pain, and fueled by the large number of patients suffering from back pain, improved diagnostic and treatment methods and devices and constantly being sought.

Back pain may be classified into two general categories: (1) "axial spinal pain," which arises from pathology or dysfunction in the structural components of the spine, such as the vertebrae or the intervertebral discs between the vertebrae; and (2) "radicular pain," which originates from pressure on or irritation of nerve roots. Radicular pain is often relatively simple to diagnose and pinpoint, because pain tends to radiate from irritated nerve roots out into the body in predictable patterns, and nerve root compression can often be seen on an MRI study or other radiological study of the spine. Treatment of radicular pain is also often quite straightforward, typically involving injections or surgical procedures to decrease inflammation in or remove the structures impinging on the effected nerve root.

In contrast to radicular pain, axial spinal pain is typically much more difficult to diagnose and localize. "Discogenic pain," for example, which is a type of spinal pain originating in one or more intervertebral discs (soft tissue structures between vertebrae of the spine), is particularly difficult to diagnose and pinpoint to one or more specific discs. The physical examination and complaints of the patient typically provide only general clues as to the actual cause and originating location of the pain, and no currently available radiological studies can accurately assess which of a patient's discs (if any) is causing discogenic pain. Adding to the difficulty of diagnosis is the fact that many different factors may lead to discogenic pain. Furthermore, it is often difficult to determine whether treatment of a disc (or discs) will actually alleviate the patient's pain or whether there are other underlying causes of the pain that will remain even after a disc is treated. Therefore, diagnosing and treating discogenic pain can often be incredibly challenging, and there is always a risk that surgery will be performed unnecessarily or will fail to relieve the patient's back pain.

The most commonly performed surgical procedure for treating discogenic pain is spinal fusion, in which adjacent vertebrae above and below the disc causing pain are fused together to prevent motion, thus bypassing the painful disc. Spinal fusion can be a very effective treatment, but it is relatively costly and invasive, and may be associated with a prolonged recovery and a number of potential complications. For example, fusion may sometimes lead to accelerated degeneration of one or more discs adjacent the treated disc due to increased forces placed on the adjacent discs from the fusion. Another possible treatment of discogenic pain involves replacement of the disc with an artificial (prosthetic) disc. This treatment may allow for better patient mobility than spinal fusion, but this treatment option is still in its infancy. Regardless of the method used to treat discogenic pain, an accurate diagnosis is essential for the treatment's success.

Despite the importance of obtaining a correct and specific diagnosis of discogenic pain, currently available diagnostic techniques have a number of drawbacks. A diagnostic test referred to as "discography" is the most commonly used and accepted diagnostic technique. Discography involves inserting a needle into an intervertebral disc and injecting a contrast dye into the compliant inner core of the disc (the nucleus pulposus) under pressure. A radiograph (or "X-ray") of the spine is then taken. Sometimes, anatomical defects of the disc, such as tears in the fibrous outer layer of the disc (the annulus fibrosis) can been seen on a radiograph, which may be indicative of a possible cause of pain. Additionally, the injection of contrast into the disc under pressure has been shown to sometimes cause the patient to feel pain, caused by the chemical composition of the contrast and/or by increased pressure within the nucleus pulposus. Sometimes this pain mimics the back pain that the patient usually feels during daily activities. Through a combination of subjective analysis of radiographs and a subjective description of the back pain by the patient, the physician attempts to determine whether the particular disc is causing the patient's pain. In some instances, multiple discs on one patient are injected during a diagnostic procedure.

Some clinicians theorize that if a discogram is positive according to commonly used criteria, then the tested disc is the source of the patient's pain. However, there is no universally accepted definition of the criteria for a positive discogram. As a result, interpretation of discograms has been a longstanding controversy. Not only does the test rely on subjective feedback, but results themselves have been shown to have a high rate of false positives and false negatives, with up to 30-40% of patients with no back pain having positive discograms. Similarly, some patients have reported feeling a replication of their usual pain during discography, even though it is later found that another, non-discogenic cause was the actual origin of the pain. These facts demonstrate that the traditional discogram is not highly specific.

A number of currently available epidural catheters and techniques provide for injecting substances, typically anesthetics, into an epidural space of a spine. Examples of such epidural catheters are described in U.S. Pat. Nos. 3,885,561; 4,737,146; 4,973,305; 5,004,456; 5,024,655; 5,084,016; 5,129,889; 5,234,406; 5,344,439; 5,800,407; 6,676,643 and 6,368,315. Such catheters, however, are not adapted for delivery into an intervertebral disc. Furthermore, injecting substances into the epidural space is not helpful for diagnosing discogenic pain.

Due to the prevalence of discogenic pain and other types of back pain, the difficulty of accurately diagnosing and pinpointing discogenic pain, and the invasive nature of typical discogenic pain treatment techniques such as spinal fusion, improved methods and apparatus for diagnosing and/or treating discogenic pain are needed. Ideally, such methods and apparatus would enhance a physician's ability to pinpoint one or more discs that are causing a patient pain, thus enhancing or replacing traditional discography. Also ideally, these methods and devices would be no more invasive, or perhaps even less invasive, than discography. Even more ideally, variations of techniques and devices for diagnosing discogenic pain could also be used to treat back pain in some individuals, thus providing less invasive alternatives to traditional spinal fusion and other surgical techniques. At least some of these objectives will be met by the present invention.

BRIEF SUMMARY OF THE INVENTION

Methods and devices of the present invention generally facilitate diagnosis, and in some cases treatment, of discogenic pain. More specifically, methods and devices of the invention help determine whether one or more intervertebral discs in a patient are actually causing the patient's back pain, and also help pinpoint which disc or discs are causing the pain. In one embodiment, a distal portion of a catheter device is positioned transannularly or transosseously in an intervertebral disc that is thought to be the cause of the patient's pain. One or more anchoring members are then used to maintain the distal portion in the disc. The patient is asked to assume a position or perform a task, such as bending over, which typically causes the patient to experience back pain. Using the catheter device, one or more substances, such as an anesthetic or analgesic, are injected into the disc. The patient then reports whether the anesthetic has alleviated the pain. Optionally, additional intervertebral discs may be tested, one or more placebo injections may be used, a conventional discography may be added to the procedure and/or the like. Based on the patient's response to the introduction of substance(s) into the disc (or discs), a determination may be made as to whether one or more specific discs are causing the patient's pain. Diagnostic and treatment decisions may be based on such a determination.

An "intervertebral disc" is generally referred to herein as soft tissue between any two adjacent vertebrae. An intervertebral disc generally includes a fibrous outer layer called the "annulus fibrosis" and a more compliant inner core called the "nucleus pulposus." In various embodiments, substances may be introduced into an annulus fibrosis, nucleus pulposus, or both. To the extent that other soft tissues between two adjacent vertebrae may also be considered part of an intervertebral disc, it is contemplated within the scope of the invention that one or more substances may be introduced into such soft tissues as well.

In some cases, devices and methods for diagnosing discogenic pain may also be used for treating pain. Catheter devices of the invention generally include one or more anchoring members for maintaining a distal portion of the catheter device in a position within a disc. Such a catheter device may be coupled with, for example, an implantable pump or injection port, and the pump or port may be used to supply one or more substances, such as anesthetic or analgesic, to the disc to treat a patient's back pain. Many other substances may be introduced to the disc, as discussed fully below, and other treatment modalities are possible, such as transcutaneous electrical nerve stimulation (TENS).

In one aspect of the present invention, a method for introducing one or more substances into an intervertebral disc involves positioning a distal portion of a catheter device in the disc, anchoring the distal portion of the catheter device to maintain the distal portion in the disc, and introducing at least one substance into the disc through the catheter device. A number of different methods for positioning the distal portion may be employed in various embodiments of the invention. In one embodiment, for example, the catheter device is passed through a lumen of an introducer device. In one such embodiment, positioning the distal portion of the catheter involves passing the catheter device through the lumen of the introducer device over a pointed stylet, piercing through an annulus fibrosis of the disc using the stylet, and withdrawing the stylet from the catheter device. In an alternative embodiment, positioning the distal portion involves piercing through an annulus fibrosis of the disc into the disc with a tapered distal end of the catheter device. In some embodiments, the catheter device is passed over a guidewire.

In various embodiments in which an introducer device is used, the introducer device may either be advanced to a position within the disc or to a position just outside the disc. In either case, the catheter device may have a distal end or portion configured to facilitate advancement of the distal end through the annulus fibrosis. In some embodiments, the catheter device is passed over a guidewire. In some cases, the catheter is passed over the guidewire within the needle, while in alternative embodiments the introducer is removed over the guidewire before the catheter device is passed over the guidewire. In some embodiments, positioning the distal portion is facilitated by visualizing at least one radioopaque marker or material at or near the distal portion to assess its location.

In some embodiments, anchoring the catheter device involves deploying one or more anchoring members disposed along the catheter body. In some cases, such anchoring members may be disposed at or near the distal portion of the catheter, while in other embodiments anchoring may occur at locations farther from the distal portion. In some embodiments, anchoring may be achieved by using a separate anchoring device, such as by applying adhesive, suture or the like to anchor the catheter to the patient in a desired position. In one embodiment, anchoring involves inflating at least a first expandable member in the disc. Optionally, this technique may further involve inflating at least a second expandable member adjacent an outer surface of the disc, such that there is one inflatable member in the disc and another inflatable member just outside the annulus fibrosis.

In an alternative embodiment, anchoring comprises deploying at least one mechanism along the distal portion of the catheter device to increase the effective cross-sectional diameter of the catheter at one or more locations. For example, in one embodiment the cross-sectional diameter is increased by releasing one or more shape memory or spring loaded members from constraint. In other embodiments, the cross-sectional diameter may be increased by actuating one or more mechanical members or moving an inner catheter shaft of the catheter device relative to an outer catheter shaft of the catheter device to cause one or more anchoring members to buckle outwards. In another embodiment, anchoring comprises causing at least part of the distal portion to change from a substantially straight shape to a substantially curved or geometric shape. And in yet another embodiment, anchoring comprises attaching part of the distal portion to an annulus fibrosis of the disc. For example, the attachment member may be screwed, twisted or pierced into the annulus fibrosis in various embodiments.

In addition to the anchor mechanisms described above, the access and treatment catheters of the present invention can be modified to promote tissue growth on or into at least selected portions of the catheter. Such tissue growth promotion could be accomplished by modifying the exterior texture or shape of the catheter exterior, or by providing additional physical structure which would promote tissue ingrowth and attachment. Alternatively or in addition, the catheter could be provided with an osteogenic substance, drug, or chemical to promote the desired tissue attachment. Such tissue attachment can be promoted in bone, muscle, fibrotic tissue, scar tissue, chondrocytes, or other tissue which occurs in or around the disc space of vertebral bodies. Anchoring by promoting tissue ingrowth is particularly useful when the catheter will be implanted for an extended length of time, as will often be the case for therapeutic treatment protocols.

The substance (or substances) introduced into the disc may be any suitable substance, typically introduced for diagnosis and/or treatment of discogenic pain, but in alternative embodiments for any other suitable purpose. Any suitable combination of substances may be introduced, either simultaneously or sequentially, for diagnosis, treatment or other purposes. In some embodiments, one or more placebo substances may be introduced into one or more discs, typically to assist in diagnosis but in other embodiments for study or experimental purposes or the like. In some embodiments, for example, introduced substance(s) may include, but are not limited to, an anesthetic; an analgesic; an antibiotic; a hydrating agent such as hypotonic saline, isotonic saline or hypertonic saline; a supportive agent such as a hydrogel, ethylene-vinyl alcohol copolymer, Dimethyl Sulfoxide or Tantalum; a prolotherapy agent such as sodium morrhuate, cod oil, phenol, minerals or ethyl alcohol; and other agents such as collagen, stem cells, Osteogenic Protein-1, ethanol, alcohol, steroids, radio-opaque contrast agents, ultrasound contrast agent, Bone Morphogenetic Protein (BMP), BMP-2, BMP-4, BMP-6, BMP-7, BMP-12, Serotonin 5-HT2A receptor inhibitors, LMP-1, TIMP-1, TGF-1, TGF-2, Rofecoxib, Ketorolac, Glucosamine, Chondroitin Sulfate, Dextrose, DMSO, non-steroidal antiinflammatory drugs, ibuprofen, naprosyn, Bextra, Vioxx, Celebrex, indomethacin, botulinum toxin, capsaicin, vanilloid agonists, vanilloid antagonists, VR1, VRL-1, steroids, methylprednisolone or chymopapain. Substances may be delivered in a biodegradable or time release vehicle to provide long-term administration of the substances.

Examples of anesthetics and analgesics include, but are not limited to lidocaine, chloroprocaine, mepivacaine, ropivacaine, xylocaine, prilocaine, morphine, bupivocaine, marcaine, 2-chloroprocain, fentanyl, diamorphine, meperidine, methadone, alfentanil, hydromorphone, lofentanil, sufentanil, buprenorphine, other opiates, adrenergic agonists, somatostatin analogs, calcium channel blockers, N-methyl-D-aspartate receptor antagonists, ketamine, benzodiazepines, klonidine, tizanidine, midazolam, levorphanol, heterocyclic antidepressants, nonheterocyclic, serotonin-enhancing antidepressants, GABA analogues, psychogenic amines, somatostatin, octreotide, SNX-111, midazolam, methylprednisolone acetate, Aristospan, ethyl chloride, etidocaine, linocaine, triamcinolone diacatate, Astramorph, Duramorph, Dilaudid, Sensorcaine MPF, Baclofen (Lioresal), Clonidine, baclofen, codeine, neurontin and Demerol. Examples of antibiotics include, but are not limited to, Penicillins, Cephalosporins, Tetracycline, Erythromycin, Clindamycin, Vancomycin, Bacitracin, Doxycycline, Ampicillin, Levaquin, Metronidazole, Azithromycin, Ciprofloxacin, Augmentin, Bactrim, TMP-SMX, Rocephin, Gentamycin, Keflex and Macrobid.

In some embodiments, the method further involves, before introducing the substance, causing the patient to assume a position in which substantial spinal pain is experienced. In such embodiments, the substance introduced is often an anesthetic or analgesic, and determining whether the patient feels the spinal pain after introduction of the substance helps determine whether pain is caused by that particular disc. Such a method may optionally further include positioning a distal portion of a second catheter device in a second intervertebral disc, anchoring the distal portion of the second catheter device to maintain the distal portion in the second disc, and introducing at least one substance into the second disc through the second catheter device. The method may also involve, before introducing the at least one substance into the second disc, causing the patient to assume a position in which substantial spinal pain is experienced, wherein the at least one substance includes at least one anesthetic or analgesic. In some embodiments, the method involves determining which of the discs into which the at least one substance was introduced is causing the patient's spinal pain. Such methods may optionally further include performing a discography procedure on the intervertebral disc before positioning the distal portion of the catheter device in the disc. Alternatively, in other embodiments the discography procedure may be performed on the intervertebral disc after introducing the at least one anesthetic.

In one embodiment of this method, the at least one substance is introduced into the disc (or into multiple discs) automatically over a period of time. This may involve, for example, coupling the catheter device with an automated injection device, which will allow the patient to rest alone in a clinic or hospital room, assume various back-pain-generating positions or the like, while various substances are being introduced into one or more discs. In some embodiments, such a method may also include recording one or more patient inputs describing back pain experienced by the patient.

Some embodiments of the method further include leaving the catheter device in position with the distal portion in the disc and administering the at least one substance over time to provide treatment of spinal pain. As mentioned previously, in some embodiments the substance(s) may be administered over time via a subcutaneous injection port or implanted pump, the method further comprising coupling the catheter device to the subcutaneous injection port or implanted pump. In alternative embodiments, the substance(s) may be administered over time via any other suitable combination of devices or other means.

In another aspect of the present invention, a method for identifying an intervertebral disc that is causing pain involves positioning a distal portion of a catheter device in a disc of a patient, anchoring the distal portion of the catheter device to maintain the distal portion in the disc, causing the patient to assume a position in which substantial spinal pain is experienced, and introducing at least one substance into the disc through the catheter. In this aspect, the method may include any of the features, steps or variations described above.

In yet another aspect of the present invention, a catheter device for introducing one or more substances into an intervertebral disc comprises an elongate flexible catheter body and at least one anchoring member disposed along the catheter body for anchoring at least part of the distal portion of the catheter in the intervertebral disc. The catheter body itself has a proximal portion, a self-introducing distal portion for facilitating penetration of an annulus fibrosis of the disc, and at least one lumen for introducing one or more substances into the intervertebral disc. By "self-introducing," it is meant that the distal portion of the catheter body has at least one feature that facilitates penetration of an annulus fibrosis by the distal portion.

In some embodiments, the anchoring member is disposed on or near the distal portion of the catheter, while in other embodiments it may be located farther from the distal portion or may even be a separate device used to anchor the catheter. In various embodiments, the anchoring member (or multiple anchoring members) of the catheter device may take any of a number of various forms. For example, in one embodiment the anchoring member comprises at least one expandable member coupled with an inflation lumen. In an alternative embodiment, the anchoring member comprises at least one shape memory, spring loaded or mechanically activated member for increasing the effective cross-sectional diameter of the catheter body at or near the distal portion. Alternatively, the anchoring member may comprise at least one outwardly buckling member coupled with an inner catheter shaft and an outer catheter shaft of the catheter body so as to outwardly buckle when the inner shaft is moved axially relative to the outer shaft. In yet another embodiment, the anchoring member comprises at least one attachment member for attaching to an annulus fibrosis of the disc. Such an attachment member, for example, may include at least one threaded surface, spiral needle or the like. In another embodiment, the anchoring member comprises at least one deformable member to change at least part of the distal portion from a substantially straight shape to a substantially curved or geometric shape.

In various embodiments, the catheter body may have any suitable configuration, dimensions, features or the like. For example, in one embodiment the self-introducing distal portion of the catheter body comprises at least one pushable portion, the pushable portion having a stiffness greater than adjacent portions of the catheter body. Optionally, the self-introducing portion may further comprise a tapered distal end of the catheter device. In some embodiments, the device may include a pointed stylet removably disposed within a lumen of the catheter device for piercing through the annulus fibrosis of the disc.

A number of features may facilitate passage of the catheter body through an introducer device. For example, in one embodiment the catheter body includes a friction resistant outer surface. In some embodiments, the outer diameter of the catheter body is less than 2 mm. Also in some embodiments, a cross-sectional diameter of the catheter body is larger near a proximal end of the body than near a distal end of the body. Optionally, the catheter body may also include an outer surface having one or more markings for indicating depth of insertion of the catheter device into a patient's body. In alternative embodiments, the catheter body may include an outer surface having two or more different colors for indicating depth of insertion of the catheter device into a patient's body. The catheter body may further include at least one radioopaque marker or material for facilitating visualization of the catheter device in a patient.

In one embodiment, the catheter device includes an injection tube extending through at least part of the lumen of the catheter body for introducing one or more substances into the disc and an inflation tube extending through at least part of the lumen for expanding the deployable anchoring member. The injection tube may be made of any suitable material or combination of materials, such as but not limited to stainless steel, tempered stainless steel, annealed stainless steel, polymers, and superelastic alloys. In some embodiments, the injection and inflation tubes exit a proximal end of the catheter body and are removably coupled with at least one adapter to provide for injection and inflation. In some embodiments, the injection and inflation tubes extend through at least part of the catheter body lumen coaxially. Alternatively, the injection and inflation tubes may extend through at least part of the catheter body lumen side-by-side. In other embodiments, the injection and inflation tubes may extend through part of the catheter body lumen coaxially and through another part of the lumen side-by-side. In an alternative embodiment of the catheter device, the catheter body does not include injection and inflation tubes but instead comprises a single extrusion having an injection lumen for introducing one or more substances into the disc and an inflation lumen for expanding the at least one anchoring member.

In various embodiments, the catheter device may have any suitable proximal end configurations for providing connection to one or more injection, inflation, suction, irrigation or other devices, for providing guidewire access and/or the like. In one embodiment, for example, a proximal end of the proximal portion of the catheter body is bifurcated into two separate catheter body proximal ends. In some embodiments, each of the two proximal ends is removably coupled with an adapter for facilitating injection or inflation via either end. Some embodiments of the device also include a guidewire having a distal end shaped to maintain the distal end within the disc. Such a distal end may include, for example, a double guidewire, a coil or a pigtail. Such guidewires can be made from any conventional guidewire material, including stainless steels and superelastic materials such as nickel-titanium alloys. Generally, the use of superelastic guidewires is preferred since other materials, such as stainless steel, may inadvertently kink in a location distal to the tip of the catheter as it is being advanced. If the guidewire kinks, it can be difficult to remove the guidewire from the catheter, interfering with the remainder of the procedure.

It will also be preferred in some instances to provide a guidewire with radioopaque markers. The guidewire will have a small diameter, and superelastic materials, such as nitinol, have low visibility under fluoroscopic imaging. The radioopacity of the guidewire can be improved by adding a radiopaque material in a variety of conventional ways. For example, the guidewire can be coated with the radioopaque material, a radioopaque core may be provided within the guidewire, a radioopaque material may be braided over the guidewire, or the material provided as ring-like markers. Such coated guidewires having improved radioopacity can be manufactured in a variety of ways, including sputtering, electroplating, electroless plating, and the like.

In another aspect of the invention, a system for introducing one or more substances into an intervertebral disc includes an introducer device and a catheter device passable through the introducer device. The catheter device includes an elongate flexible catheter body and at least one deployable anchoring member disposed along the catheter body for anchoring at least part of the distal portion of the catheter in the disc. The catheter body includes a proximal portion, a self-introducing distal portion for facilitating penetration of an annulus fibrosis of the disc, and at least one lumen for introducing one or more substances into the intervertebral disc. In various embodiments, the catheter device may include any of the features, configurations or combinations described above.

In some embodiments, the system further includes a pointed stylet removably disposed within a lumen of the catheter device for piercing through the annulus fibrosis. In some embodiments, the system includes a guidewire over which the catheter device may be passed within the introducer device. The catheter device and introducer device may have any suitable dimensions, but in one embodiment the outer diameter of the catheter body is less than 2 mm. An inner diameter of the needle, in some embodiments, is between about 0.1 mm and about 0.01 mm larger than the outer diameter of the catheter body.

In some embodiments, the system may further include an automatic injection device removably coupled with the catheter device for automatically introducing the at least one substance into the disc. These or other embodiments may optionally further include a recording device for recording patient inputs describing pain felt by a patient.

In another aspect of the present invention, a kit for introducing one or more substances into an intervertebral disc includes a catheter device, at least one implantable device removably couplable with the catheter device for introducing the one or more substances into a disc over time, and instructions for using the catheter device and implantable device. The catheter device includes: an elongate flexible catheter body having a proximal portion, a self-introducing distal portion for facilitating penetration of an annulus fibrosis of the disc, and at least one lumen for introducing one or more substances into the intervertebral disc; and at least one anchoring member disposed along the catheter body for anchoring at least part of the distal portion of the catheter within the disc. This catheter device may have any of the features described above.

The implantable device may include any of a number of suitable devices in various embodiments. For example, in some embodiments the implantable device comprises a pump. In other embodiments, the implantable device comprises an injection port.

In various embodiments, the kit may also include one or more additional devices, such as but not limited to an introducer device for facilitating positioning of the catheter device in the disc, a pointed stylet removably disposed within a lumen of the catheter device for piercing through the annulus fibrosis and/or a guidewire passable through the needle.

These and other aspects and embodiments of the present invention are described more fully below with reference to the attached drawing figures.

DETAILED DESCRIPTION OF THE INVENTION

Methods, devices and systems of the present invention generally provide for introduction of one or more substances into an intervertebral disc to facilitate diagnosis and/or treatment of discogenic pain (i.e., back pain originating in one or more intervertebral discs). Methods, devices and systems may be used alone or in conjunction with other methods or devices that are currently known or hereafter developed, such as discography, radiological studies, physical examination and/or the like. In alternative embodiments, methods and devices of the invention may be used for purposes other than diagnosis or treatment, such as for study or experimental purposes or the like. Therefore, although the following description focuses on diagnostic and therapeutic applications, various embodiments may be used for any other suitable application.

Figure 1A:
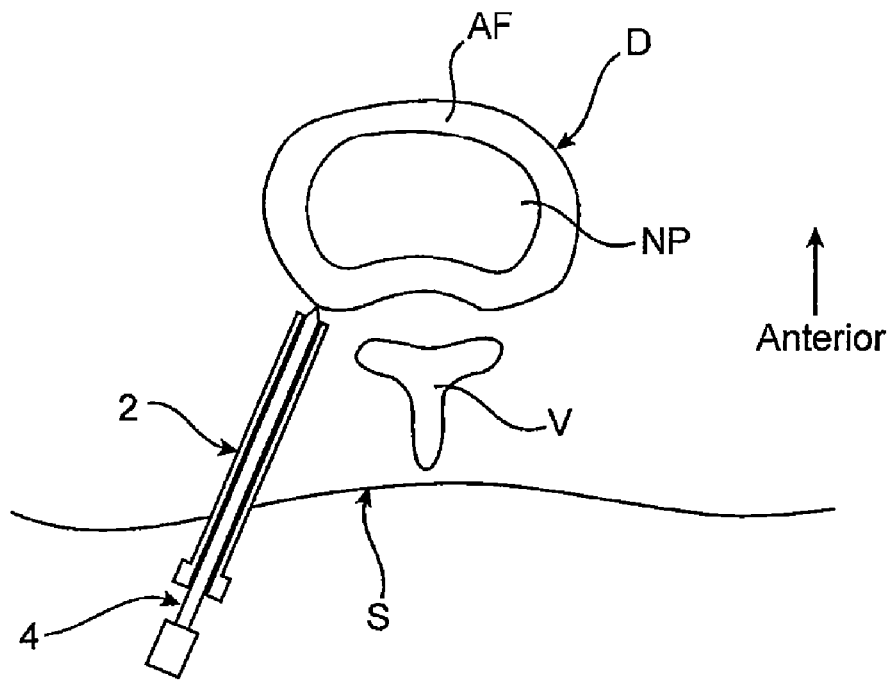
FIGS. 1A-1K illustrate a method for positioning a catheter device to introduce a substance into an intervertebral disc, shown from a transverse cross-section of the spinal column, according to one embodiment of the present invention.

Referring now to FIGS. 1A-1K, a method for introducing a substance into an intervertebral disc is illustrated schematically. As seen in FIG. 1A, an intervertebral disc D includes an annulus fibrosis AF surrounding a nucleus pulposus NP, and is positioned adjacent a spinous process of a vertebra V. Anatomically, the disc D is sandwiched between two vertebrae of the spine (not shown), which lie on top of and beneath the disc D.

In one embodiment, an introducer device 2 and a pointed obturator 4 are introduced together through the skin S of a patient's back to position their distal ends near the intervertebral disc D. Introducer device 2 and obturator 4 may have any suitable dimensions, but in one embodiment introducer device 2 is about 18-22 gauge and obturator 4 is about 20-25 gauge.

Figure 1B:
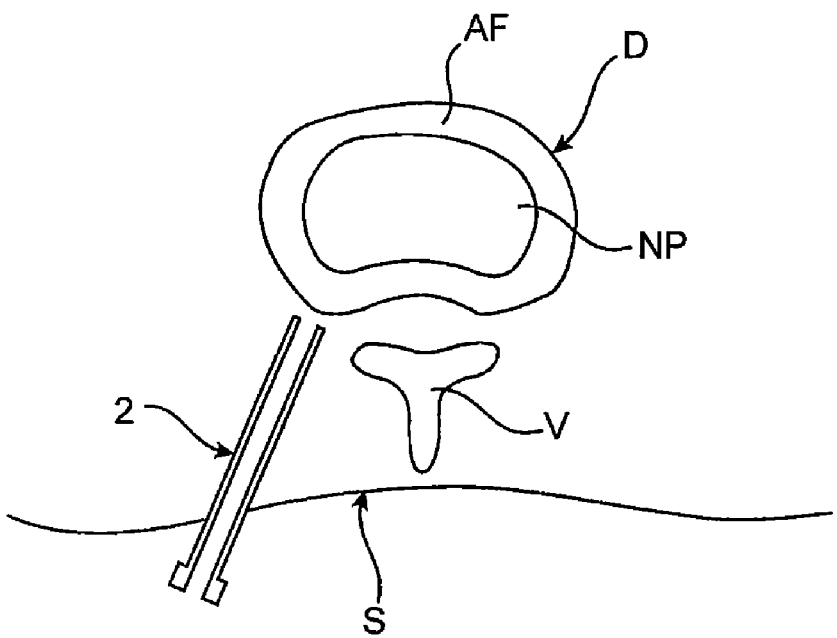
Figure 1C:
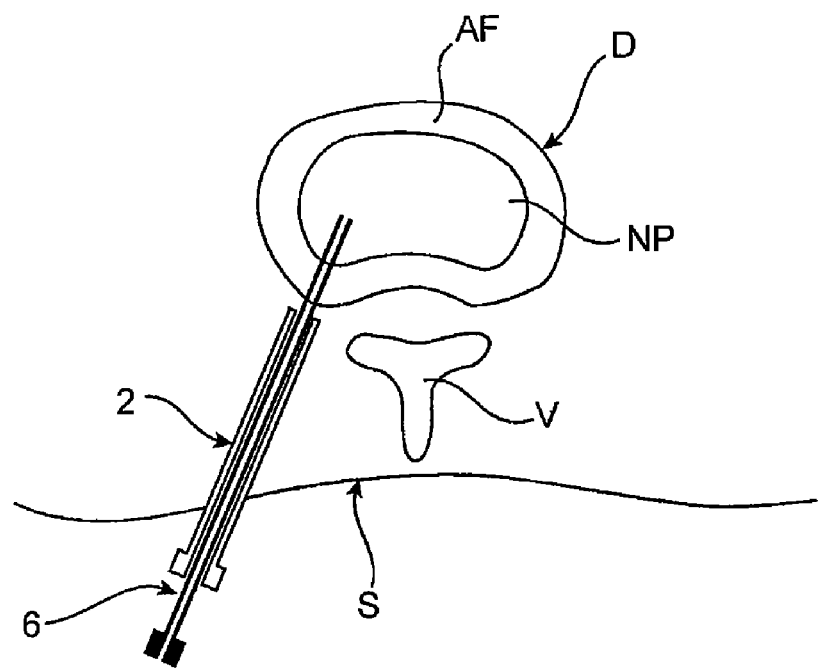

As shown in FIG. 1B, obturator 4 is then removed, leaving introducer device 2 in place. As shown in FIG. 1C, an injection needle 6 is then passed through introducer device 2 and through the annulus fibrosis AF to position its distal tip in the nucleus pulposus NP. Position of introducer device 2 and/or injection needle 6 may be confirmed using x-ray, fluoroscopy, or other suitable means. In some embodiments, when injection needle 6 is positioned in the nucleus pulposus NP, contrast dye may be injected through injection needle 6, and the appearance of the contrast dye in the disc as well as the patient's response to the injection may be monitored. This part of the procedure generally describes a known discography procedure. In alternative embodiments, discography may be performed at a later time or no discography may be performed.

Figure 1D:
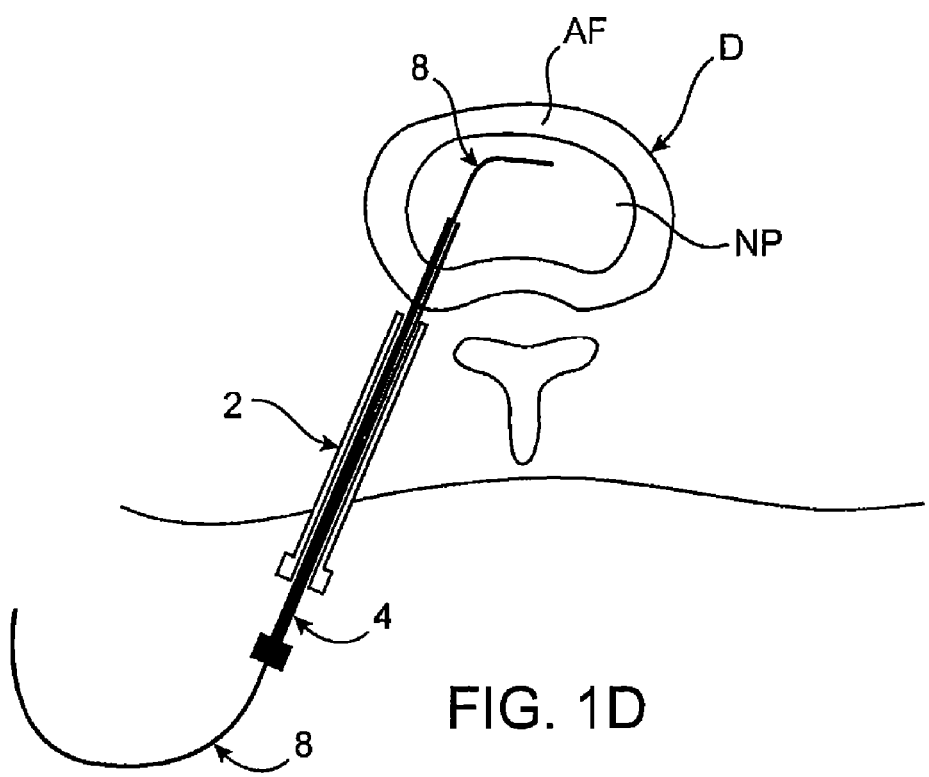
Figure 1E:
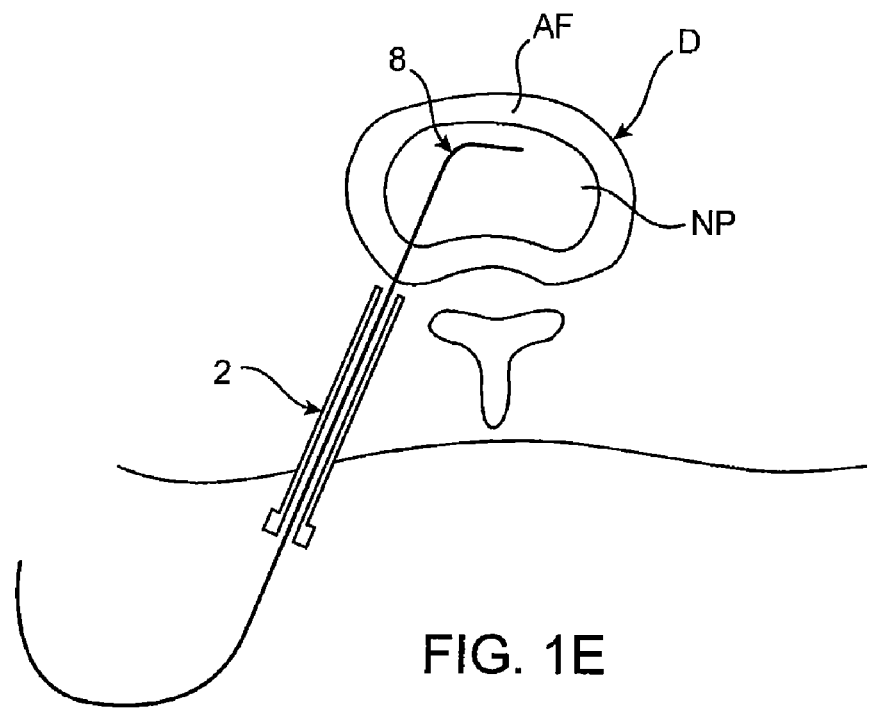
Figure 1F:
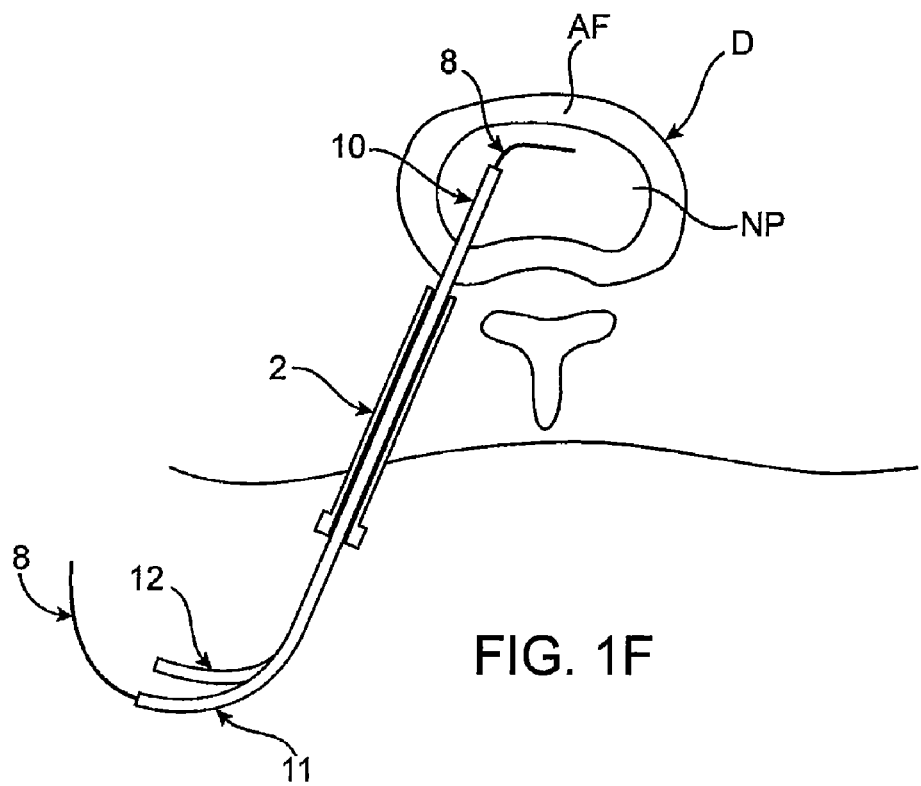
Figure 1G:
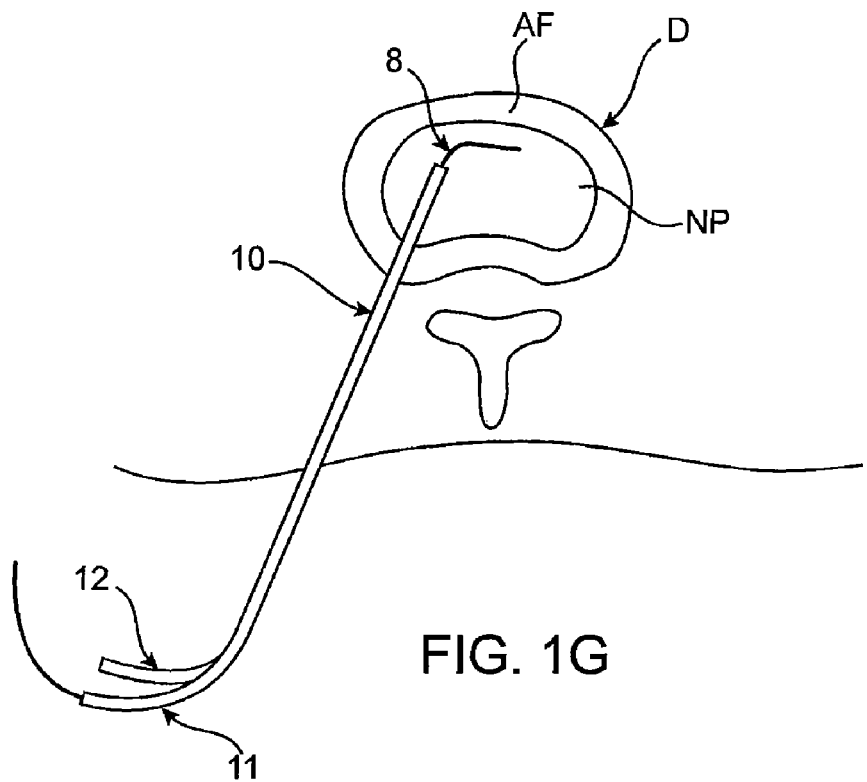
Figure 1H:
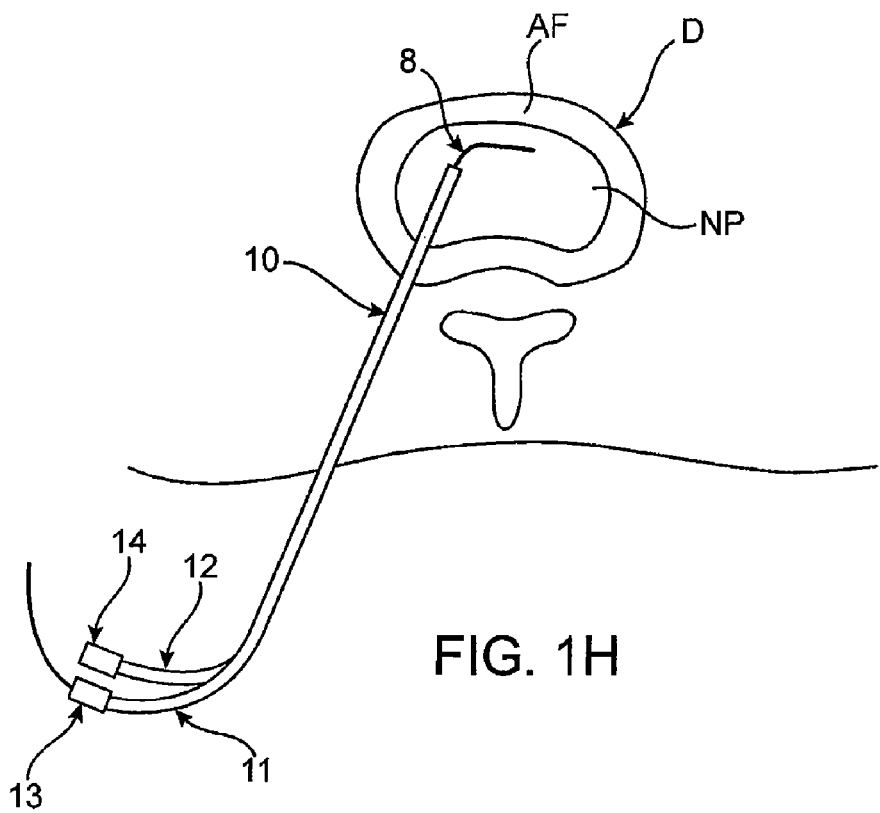

After placing injection needle 6, a guidewire 8 may be passed through injection needle 6 into the disc, as shown in FIG. 1D. Injection needle 6 may then be removed, as shown in FIG. 1E, and a catheter device 10 may be passed over guidewire 8 through introducer device 2, as shown in FIG. 1F. Catheter device 10 is described in further detail below, but in one embodiment it may include two or more tubes, such as a guidewire tube 11 and an injection or inflation tube 12, which may separate proximally to attach to multiple adapters or the like. Once catheter device 10 is in place, introducer device 2 may be removed, as shown in FIG. 1G, and adapters 13 and 14 may be coupled with the proximal ends of tubes 11 and 12. Adapters 13, 14 may facilitate guidewire passage, inflation of an expandable member, injection of one or more substances into the disc and/or the like.

Figure 1I:
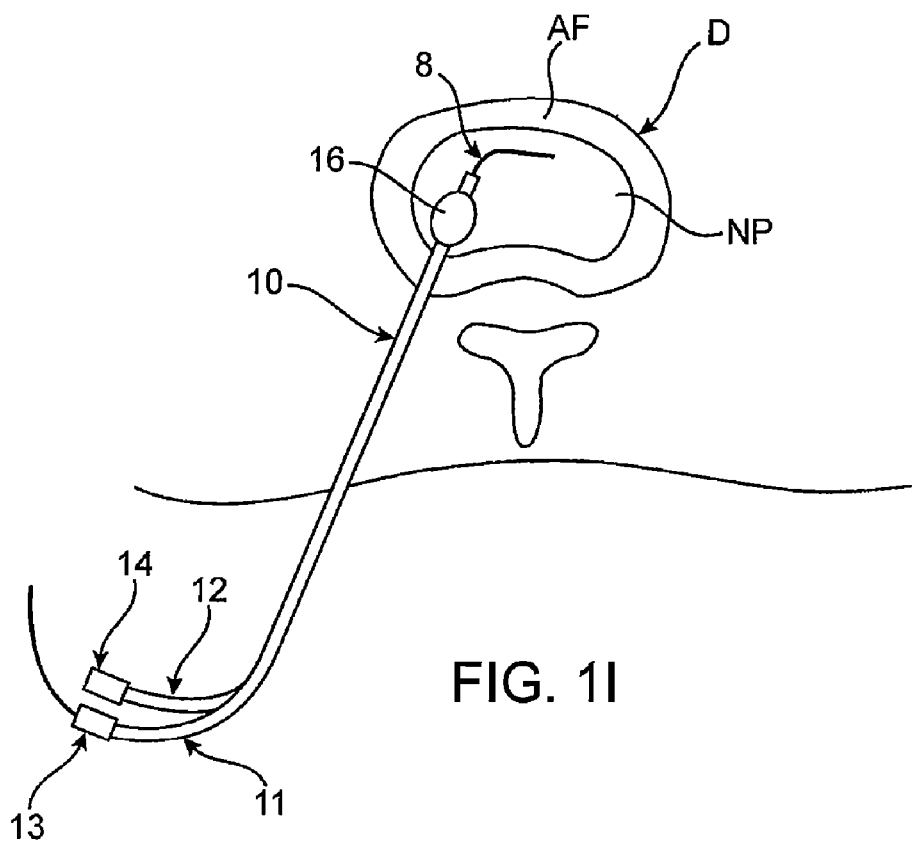
Figure 1J:
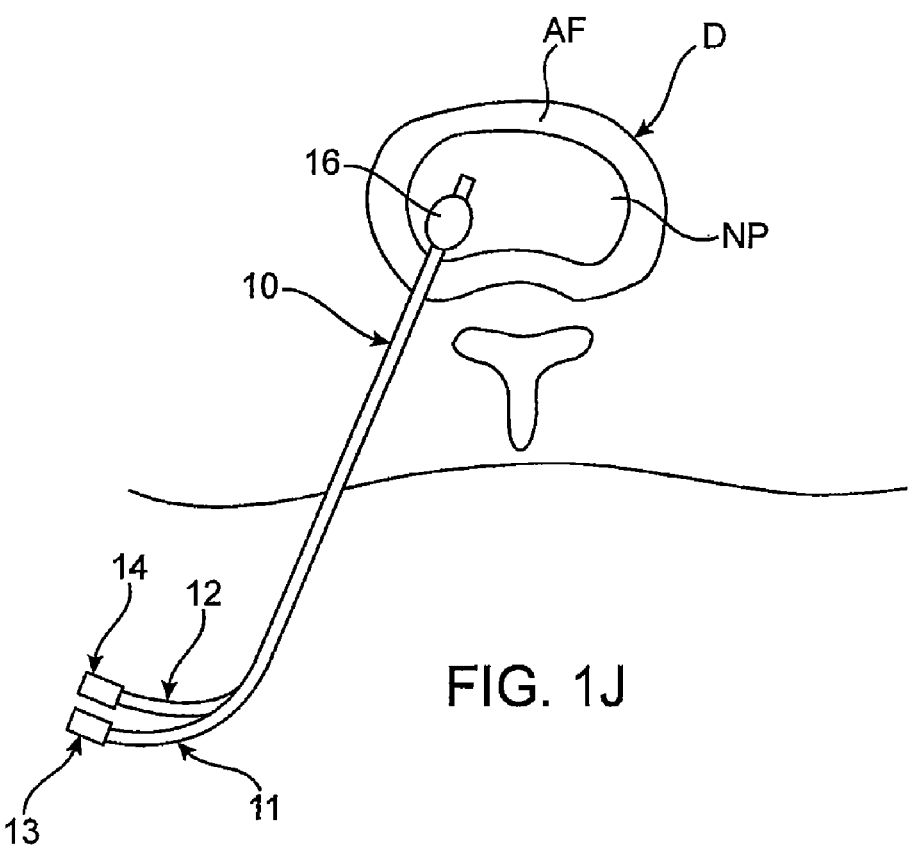
Figure 1K:
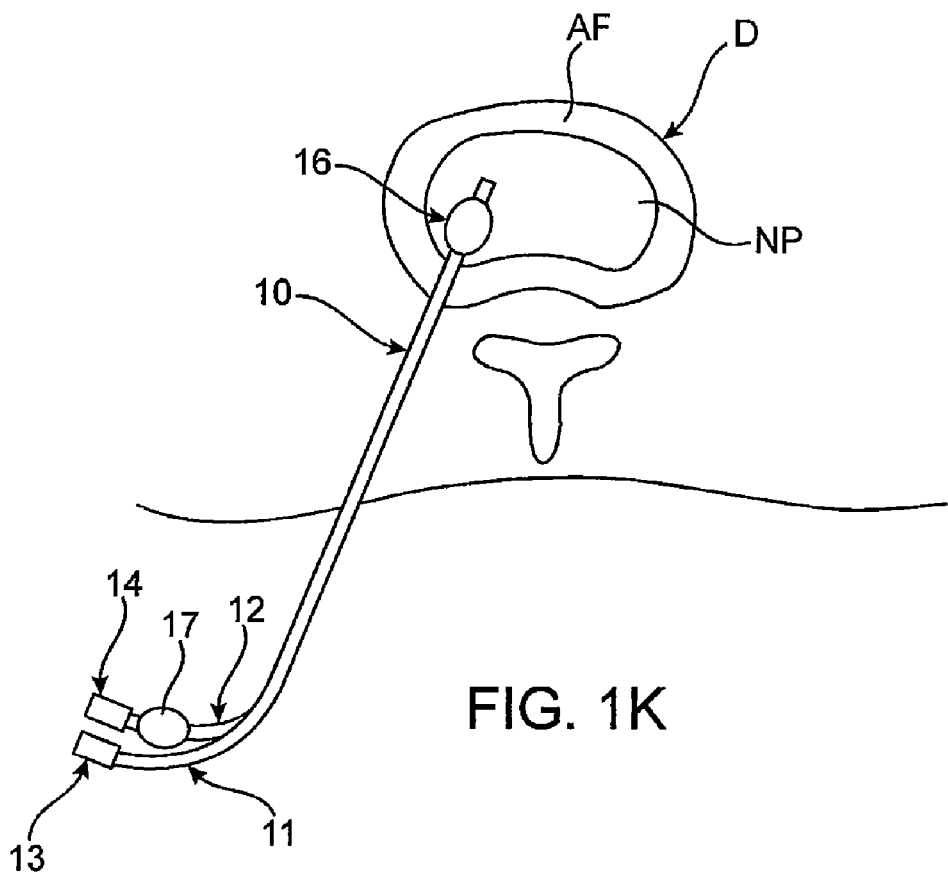

Referring to FIG. 1I, one or more anchoring members 16 disposed along catheter 10 are deployed to maintain a distal portion of catheter 10 in the disc. In one embodiment, anchoring member 16 comprises an expandable balloon, but as is described in more detail below, many other types of anchoring members may be used in various alternative embodiments. As shown in FIG. 1J, once anchoring member 16 is deployed, guidewire 8 may be removed. In some embodiments, as in FIG. 1K, a marker expandable member 17 may be deployed outside the patient's body. With anchoring member 16 and thus the distal portion of catheter 10 in place in the disc, one or more substances are introduced into the disc through catheter 10.

Figure 1L:
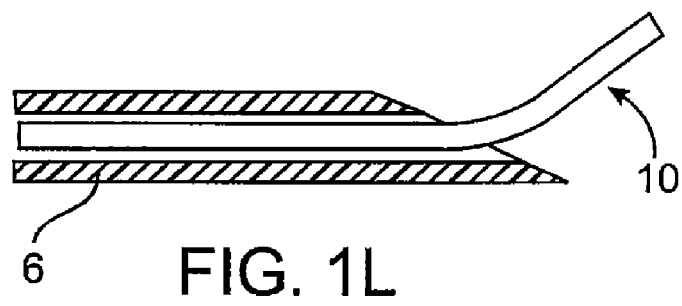
FIGS. 1L and 1M illustrate catheter introduction needles having sharpened tips (FIG. 1L) and atraumatic tips (FIG. 1M).
Figure 1M:
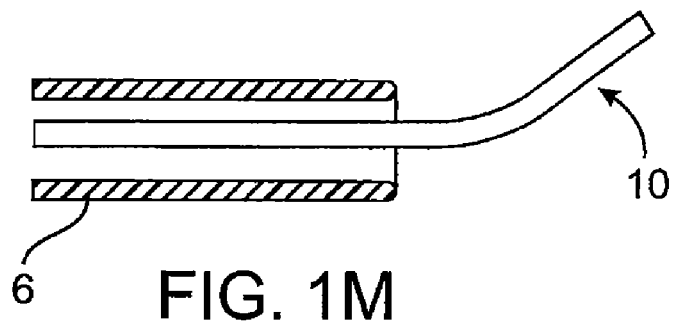
Figure 1N:
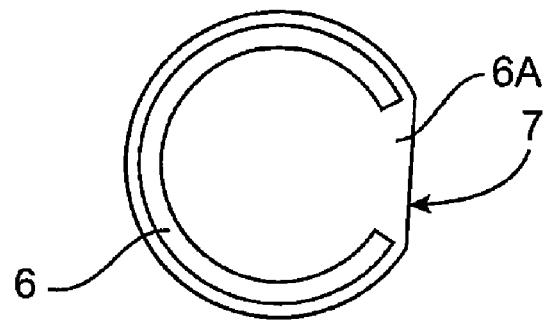
FIG. 1N illustrates a catheter-introducing needle having an axial slot and frangible cover to facilitate removal of the needle from over the catheter after the catheter has been implanted.

It may sometimes be desired to leave the needle 6 which introduced the catheter into the disc space in place to facilitate advancing and retracting the catheter. Use of a conventional needle having a sharpened tip as illustrated in FIG. 1L, however, presents a risk of damaging the catheter, particularly as the catheter may be retracted proximally through the needle. Thus, it may be preferred to employ an introducer "needle" having a blunt, rounded, or other atraumatic tip, as illustrated in FIG. 1M. In one embodiment, the atraumatic tip can be square-cut and the edges rounded to form a smooth surface which will not damage the catheter as it is advanced or retracted through the lumen of the needle. The tip could also be made of a softer material, a more flexible material, be coated with a lubricious material or otherwise modified to reduce the risk of damaging the catheter. When using a needle having an atraumatic tip, the needle may be introduced using a stylet having a sharpened tip.

When the catheter is delivered through a needle, either a sharpened needle as illustrated in FIG. 1L or atraumatic needle as illustrated in FIG. 1M, it will often be desirable to remove the needle. If the catheter has a proximal hub or other enlarged features, it may not be possible to draw the needle proximally over the enlarged structure. In such cases, it will often be desirable to use a needle 6 having an axial slot 6A, optionally covered by a frangible outer sheath, cover, or tube 7. The width of the slot 6A will be sufficient to permit the catheter to pass, and the outer tube or sheath 7 prevents accidental passage of the catheter through the slot 6A while the catheter is being introduced. Thus, the material of the tube 7 should be strong enough to contain the catheter during delivery, but still provide for easy longitudinal tearing when it is desired to withdraw the needle over the catheter. Suitable materials include polyester, PET, FEP, PTFE, polyolefins, nylons, PVCs, neoprenes, and other materials. Many of the materials may be heat-shrunk over the needle shaft. The needle shaft will typically be a metal, such as stainless steel or nitinol, but could also be composed of a polymer having sufficient strength such as a polycarbonate, a polyethylene, PEEK, a nylon, a polypropylene, or the like. The axial slot 6A may be formed in the needle by cutting or machining the opening, typically for metal needle shafts, or by extruding the material that has a C-shaped cross-section, typically for polymers. Although usually being straight, the longitudinal opening 6A could have other geometries, such as spiral, zigzag, or other arbitrary shape. The outer tube 7 may be opened by tearing, shearing, and the like, and may be pre-scored, perforated, or otherwise weakened to assist in separation. In addition to heat-shrinking, the outer tube could be attached to the shaft of the needle by melting, adhesives, or the like.

The method just described is but one embodiment of a technique for placing and anchoring a distal portion of a catheter within a disc and introducing a substance therein. In various alternative embodiments, any number of suitable changes to the technique, such as additions or deletions of various steps, use of varied devices and the like, may be made without departing from the scope of the present invention.

Figure 2A:
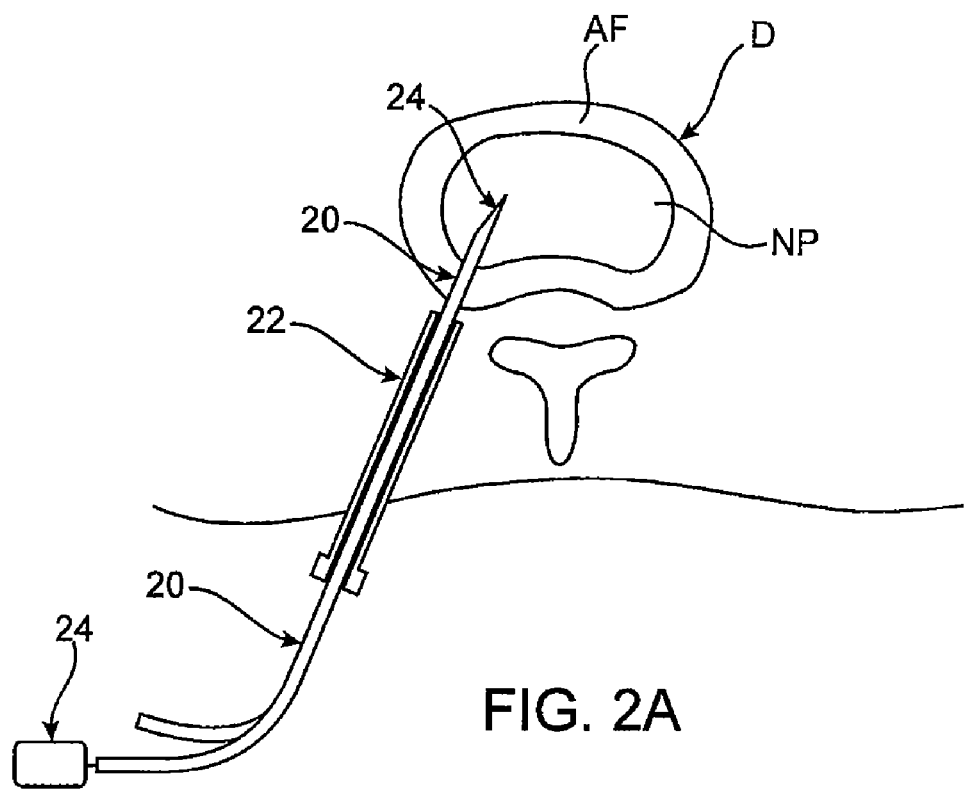
FIGS. 2A and 2B illustrate part of a method for positioning a catheter device to introduce a substance into an intervertebral disc using a pointed stylet, according to one embodiment of the present invention.
Figure 2B:
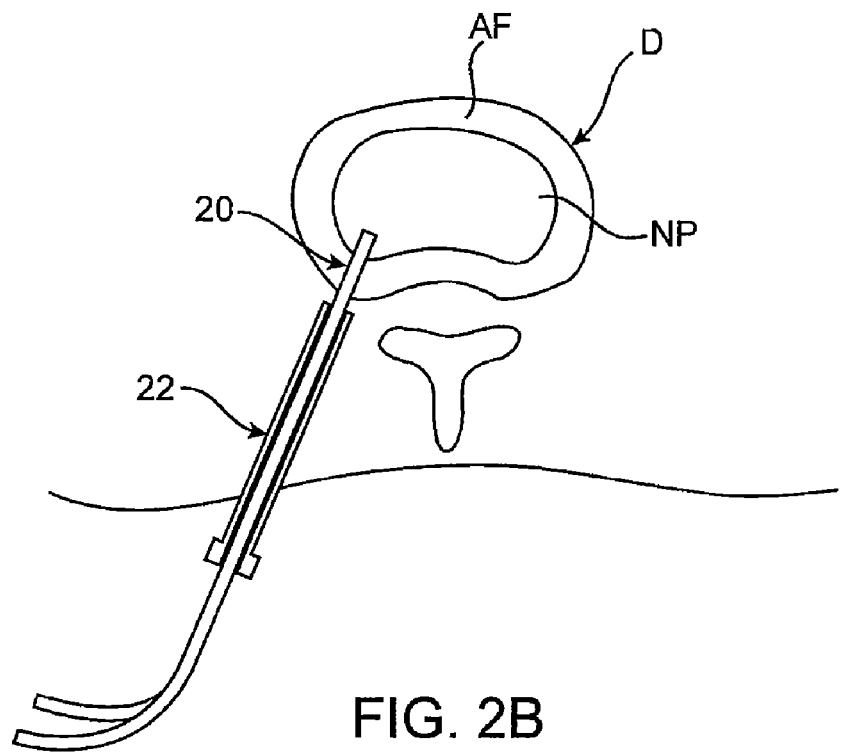

FIGS. 2A and 2B illustrate part of an alternative embodiment of a method for passing a catheter device 20 into a disc for introducing one or more substances. In this embodiment, rather than employing a guidewire passed through an injection needle, catheter device 20 is passed through an introducer device 22 with a pointed stylet 24 extending through a lumen of catheter 20 and out its distal tip. Stylet 24 enables catheter 20 to be passed through the tough annulus fibrosis AF without the help of a guidewire and injection needle. Stylet 24 is then removed, as shown in FIG. 2B, to leave catheter 20 in position for anchor deployment and substance introduction.

Stylets such as illustrated in FIGS. 2A and 2B are usually much more rigid in both the axial and bending directions than the catheter which is being advanced. The catheter can freely slide relative to the stylet. There is a risk that the catheter will differentially deflect and separate from the stylet. In order to prevent such separation, the tips of the stylet and the catheter can be modified to hold them together. For example, the stylet 24 may have a step or other geometry at its distal end which mates with a complementary shape formed inside the distal tip of the catheter 20, as illustrated in FIG. 2D. Alternatively, the stylet 24 may have a tapered or cone-shaped distal end which mates with a similar shape in the distal end of the catheter 20, as illustrated in FIG. 2E. The distal ends of the catheter and the stylet could also be modified to have mating threaded ends for a more secure but still releasable attachment.

Optionally, the distal tips of the stylets may be made to be radioopaque in order to enhance fluoroscopic imaging. For example, at least the distal portions of the stylets 24 could be composed at least partly, or plated with, a radioopaque material such as platinum, iridium, or gold. The remaining portions of the stylet may be made from stainless steel, nitinol, or other materials having the desired column strength and flexibility to provide for "pushability" of the combination of stylet 24 and catheter 20. By providing a stylet tip which is inherently radioopaque, the number of components and the profile or cross-section of the combined device (including both the stylet 24 and catheter 20) may be reduced. Reducing profile is advantageous, since it facilitates entry into the disc space through the annulus fibrosis.

Figure 2C:
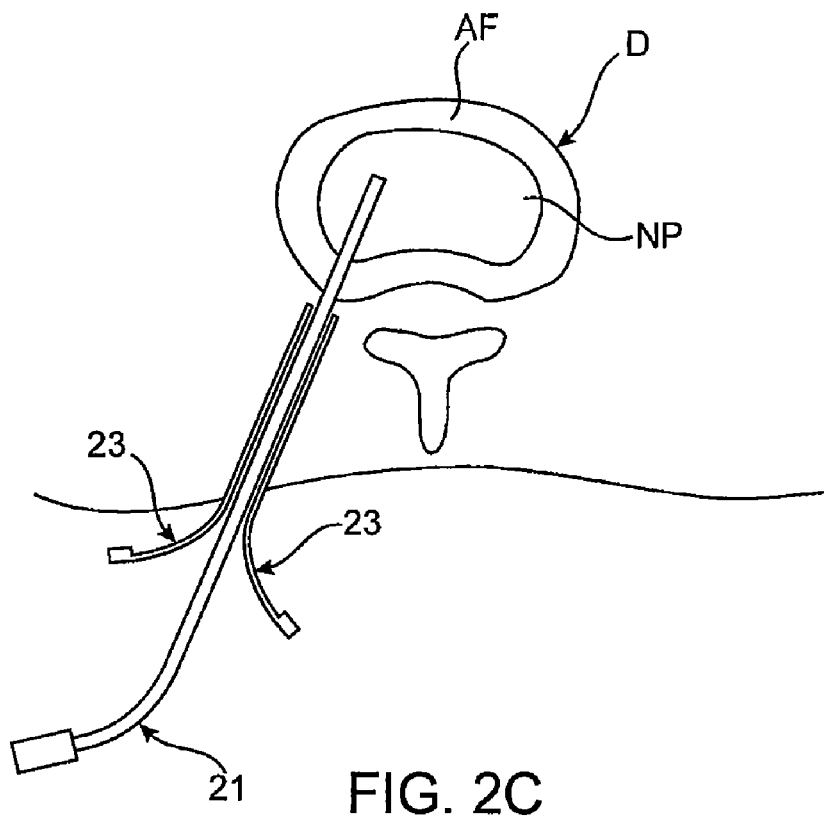
FIG. 2C illustrates a catheter device in place for introducing a substance into an intervertebral disc and an introducer device being split, according to another embodiment of the present invention.
Figure 2D:
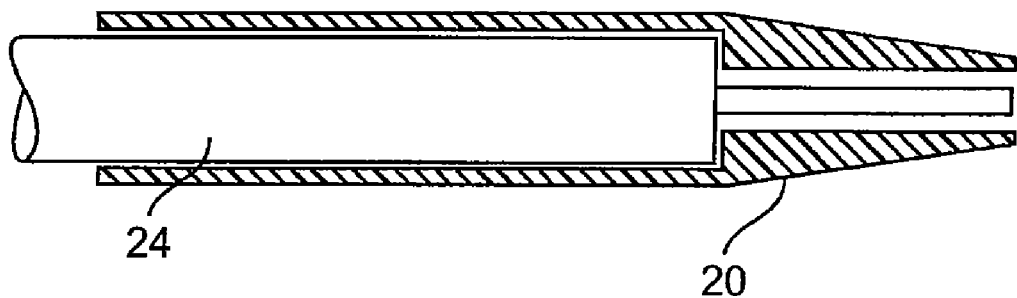
FIGS. 2D and 2E illustrate catheters and stylets having modified distal ends to enhance coupling during introduction of the catheter and stylet assemblies.
Figure 2E:
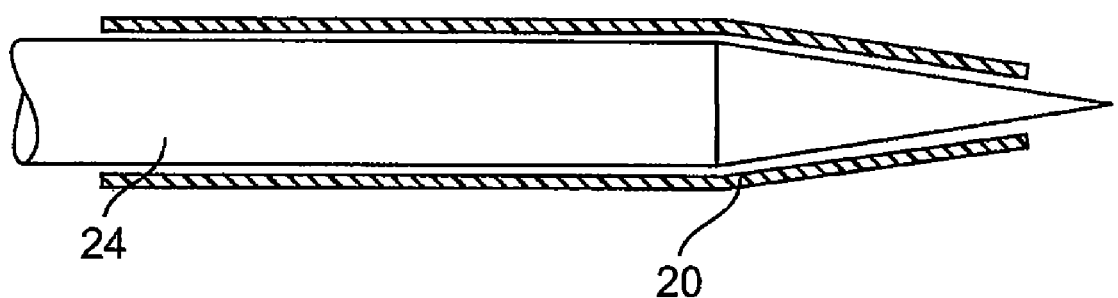

Referring now to FIG. 2C, a method for introducing a catheter device 21 into a disc to inject one or more substances may be facilitated in one embodiment through use of a split-away introducer device 23. Split-away introducer device 23 may be used just as the introducer devices have been described above. Rather than removing split-away introducer device 23 by sliding it off the proximal end of catheter device 21, however, split-away introducer device 23 is split along its length to be removed from catheter device 21. Split-away introducer device 23 may be constructed from any suitable material or materials so as to readily tear, crack, fissure, rip or separate along the length of needle 23. Splitting may be accomplished by including a perforation, thin section or other weakness along the length of needle 23.

Typically, once a catheter device is in place, with a distal portion residing in a disc and one or more anchoring members deployed to maintain the catheter's position, the patient is instructed to assume a position or perform a task that typically causes the patient pain, such as bending over to pick up an object or the like. A substance is then introduced into the disc, and the patient is asked to relate whether pain is lessened, eliminated, remains the same or the like. In various embodiments, the patient is asked to rate the experienced pain on a scale of 1 to 10 before and after introduction of substances into the disc. In one embodiment, the substance introduced is an anesthetic or analgesic, and thus may alleviate the patient's pain if injected into the disc that is actually causing the pain. In some instances multiple injections are performed, and one or more injected substances may be placebos, to test the accuracy of the test results. Again, such testing may be performed either alone or before or after traditional discography. In some embodiments, multiple discs of one patient may be accessed and tested. Also in some embodiments, testing may be performed over a prolonged period of time, to test multiple discs and/or to enhance the accuracy or certainty of test results.

In various embodiments, any of a number of different substances may be introduced into a disc. For different purposes, such as diagnosis or treatment of discogenic pain, study purposes or experimentation or the like, introduction of different substances may be warranted. Examples of possible substances that may be introduced into a disc include, but are not limited to anesthetics; analgesics; antibiotics; hydrating agents such as hypotonic saline, isotonic saline or hypertonic saline; supportive agents such as a hydrogel, ethylene-vinyl alcohol copolymer, Dimethyl Sulfoxide or Tantalum; prolotherapy agents such as sodium morrhuate, cod oil, phenol, minerals or ethyl alcohol; and/or other agents such as collagen, stem cells, Osteogenic Protein-1, ethanol, alcohol, steroids, radio-opaque contrast agents, ultrasound contrast agent, Bone Morphogenetic Protein (BMP), BMP-2, BMP-4, BMP-6, BMP-7, BMP-12, Serotonin 5-HT2A receptor inhibitors, LMP-1, TIMP-1, TGF-1, TGF-2, Rofecoxib, Ketorolac, Glucosamine, Chondroitin Sulfate, Dextrose, DMSO, non-steroidal antiinflammatory drugs, ibuprofen, naprosyn, Bextra, Vioxx, Celebrex, indomethacin, botulinum toxin, capsaicin, vanilloid agonists, vanilloid antagonists, VR1, VRL-1, steroids, methylprednisolone or chymopapain. Substances may be delivered in a biodegradable or time release vehicle to provide long-term administration of the substances.

Examples of anesthetics and analgesics include, but are not limited to lidocaine, chloroprocaine, mepivacaine, ropivacaine, xylocaine, prilocaine, morphine, bupivocaine, marcaine, 2-chloroprocain, fentanyl, diamorphine, meperidine, methadone, alfentanil, hydromorphone, lofentanil, sufentanil, buprenorphine, other opoids, adrenergic agonists, somatostatin analogs, calcium channel blockers, N-methyl-D-aspartate receptor antagonists, ketamine, benzodiazepines, klonidine, tizanidine, midazolam, levorphanol, heterocyclic antidepressants, nonheterocyclic, serotonin-enhancing antidepressants, GABA analogues, psychogenic amines, somatostatin, octreotide, SNX-111, midazolam, methylprednisolone acetate, Aristospan, ethyl chloride, etidocaine, linocaine, triamcinolone diacatate, Astramorph, Duramorph, Dilaudid, Sensorcaine MPF, Baclofen (Lioresal), Clonidine, baclofen, codeine, neurontin and Demerol. Examples of antibiotics include, but are not limited to, Penicillins, Cephalosporins, Tetracycline, Erythromycin, Clindamycin, Vancomycin, Bacitracin, Doxycycline, Ampicillin, Levaquin, Metronidazole, Azithromycin, Ciprofloxacin, Augmentin, Bactrim, TMP-SMX, Rocephin, Gentamycin, Keflex and Macrobid.

As already mentioned, in some embodiments the method further includes leaving the catheter device in place to provide treatment of a patient's back pain, such as with anesthetic or analgesic agent(s) or other substances. In some embodiments, the catheter device may be coupled with an implantable pump, injection port or other device to provide such treatment.

Figure 3A:
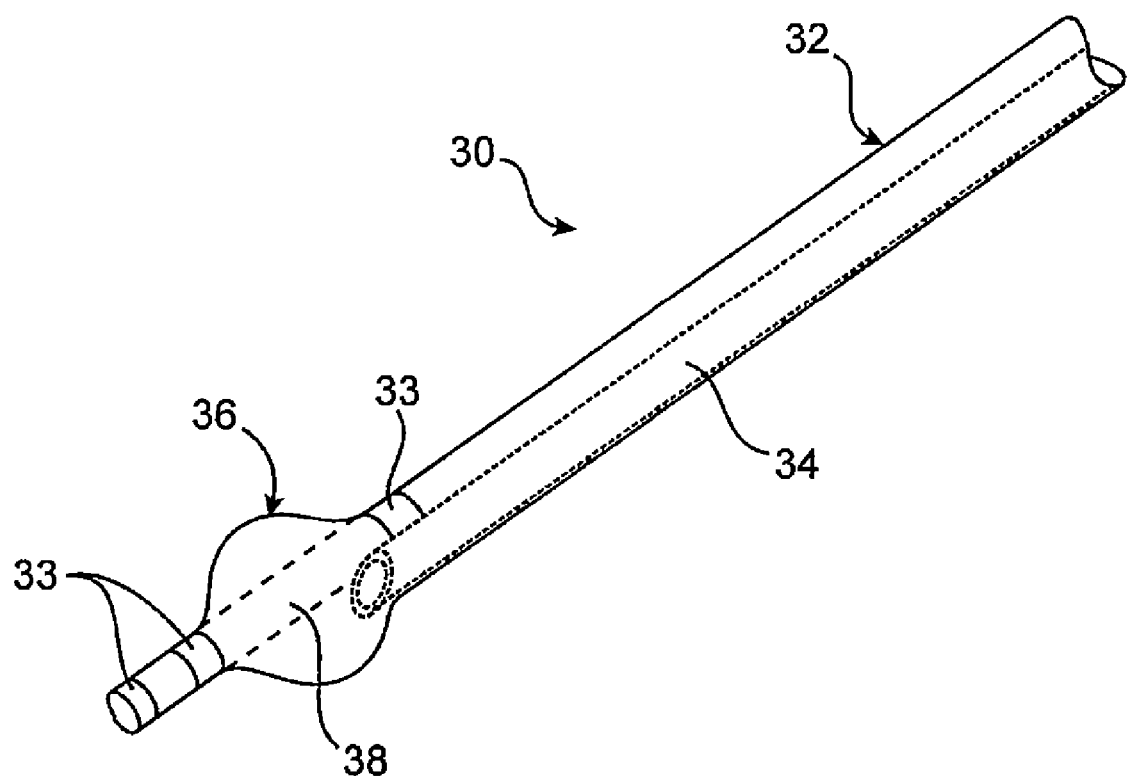
FIGS. 3A and 3B are perspective and cross-sectional views, respectively, of a distal end of a catheter device, according to one embodiment of the present invention.
Figure 3B:
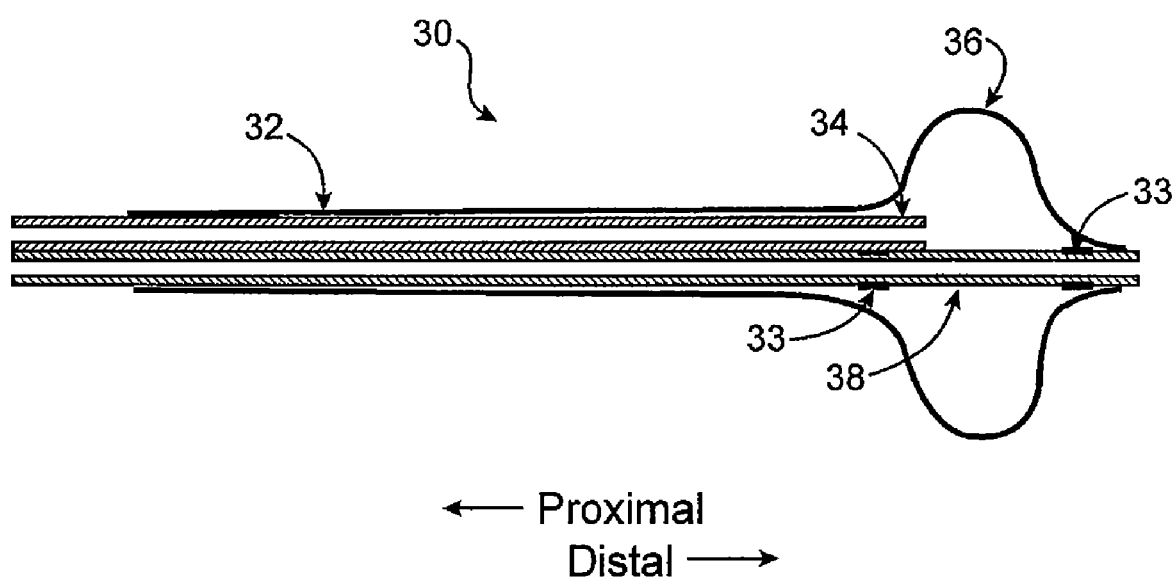

Referring now to FIGS. 3A and 3B, a distal portion of a catheter device 30 according to one embodiment is shown in perspective view and cross-sectional view, respectively. Catheter device 30 suitably includes a catheter body 32, which includes an expandable anchoring member 36, houses an inflation tube 34 and an injection tube 38, and has several radioopaque markers 33 disposed along its distal portion. Anchoring member 36 enables a distal portion of catheter device 30 to be maintained in a position within a disc. Inflation tube 34 is used to expand anchoring member 36, which in the embodiment shown comprises an expandable balloon. Injection tube 38 is used to introduce one or more fluids into the nucleus pulposus of the disc. Radioopaque markers 33 facilitate visualization of the distal portion of catheter device 30 so that its location may be assessed before, during or after a diagnostic or therapeutic procedure.

In various embodiments, the distal portion of catheter device 30 may have one or more features that facilitate advancement of the distal portion through an annulus fibrosis of an intervertebral disc. A distal portion having one or more such features is generally referred to as "self-introducing." Therefore, by "self-introducing" it is meant simply that the distal portion has one or more features for facilitating its passage through annulus fibrosis tissue. Such features may include, for example, one or more sections on a catheter shaft that are stiffer than adjacent sections to help make the shaft pushable. Another feature may comprise a tapered or pointed distal tip for piercing through annulus fibrosis. In some embodiments, catheter device 30 may be coupled with a removable, pointed stylet. These or any other suitable features may be included in a distal portion of catheter device 30 for facilitating passage through an annulus fibrosis.

The various components of catheter device 30 may be constructed from any suitable materials and may have any suitable shapes, sizes, dimensions or the like in various embodiments. In one embodiment, for example, the cross-sectional diameter of catheter body 32 decreases along its length from its proximal end to its distal end. Such a tapered configuration may allow catheter device 30 to be easily introduced through an introducer device. The outer diameter of catheter body 32 will also generally be slightly smaller than an inner diameter of an introducer device. In one embodiment, for example, catheter body 32 has an outer diameter of about 2 mm or less along at least part of its length.

In various embodiments, catheter body 32 may comprise a rigid single polymer or a composite consisting of reinforced metallic or polymeric components. Metallic components may include, for example, stainless steel, nitinol or other superelastic alloys. Polymers may include, but are not limited to Polyetheretherketone (PEEK), Polyether Block Amide (PEBAX), Nylon, Polyester, Polyolefin, polyamide, Polyimide, Polycarbonate, Polypropylene, Fluorinated Ethylene Polymer (FEP), Perfluoroalkoxy (PFA), Polytetrafluoroethylene-Perfluoromethylvinylether (MFA), Polyurethane or Low density polyethylene (LDPE). Such materials may be reinforced with coils or braids in some embodiments. The materials may also be coated internally or externally with materials the resist friction such as Teflon (Poly-Tetra-Fluoro-Ethylene), hydrophilic materials, parylene or the like.

In various embodiments, catheter shaft may include one or more radiopaque markers 33 and/or may be made from one or more radiopaque materials to facilitate visualization. Such radiopaque markers/materials may include, but are not limited to, gold, Platinum, Iridium, Tungsten, Tantulum, resins containing Barium Sulfate, Bismuth trioxide or Tungsten and/or the like.

Anchoring member 36 may also be made of any suitable materials now known or discovered in the future, according to various embodiments. For example, expandable anchoring member 36 may comprise flexible polyvinyl chloride (PVC), Polyethylene, Polyether Block Amide (PEBAX), Polyethylene Terepthalate (PET), Polyester, Nylon, Polyurethanes, Polyether Block Amide (PEBAX), Polyolefins or any suitable combination thereof. Various adhesives may be used to attach anchoring member 36 to catheter shaft 32 or for any other suitable purpose. Any suitable adhesive(s) may be used, such as but not limited to, light activated acrylics, light activated cyanoacrylates, light activated silicones, heat activated adhesives, ambient curing adhesives, cyanoacrylates, epoxy adhesives, and/or polyurethane adhesives. Various parts of catheter device 30 may also be attached using alternative means, such as friction fitting, snap fitting, screw fitting, application of energy such as thermal or radiofrequency energy, and/or the like.

Figure 4A:
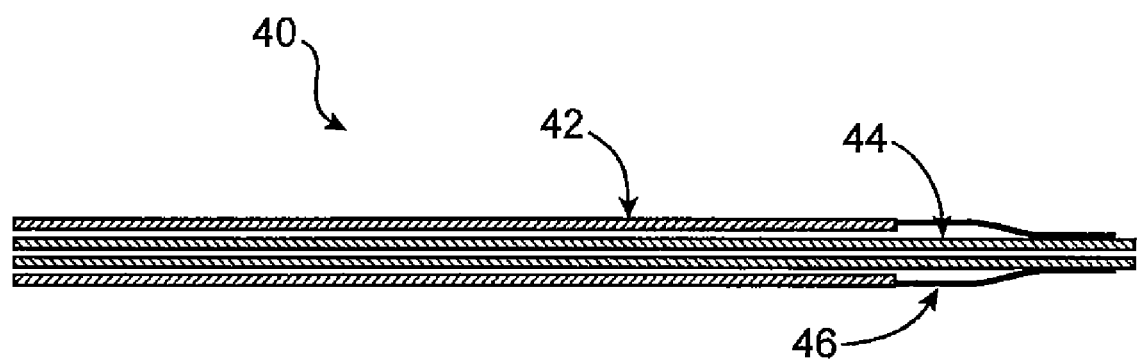
FIGS. 4A and 4B are cross-sectional views of a distal end of a catheter device with an anchoring member in an undeployed and deployed state, respectively, according to one embodiment of the present invention.
Figure 4B:
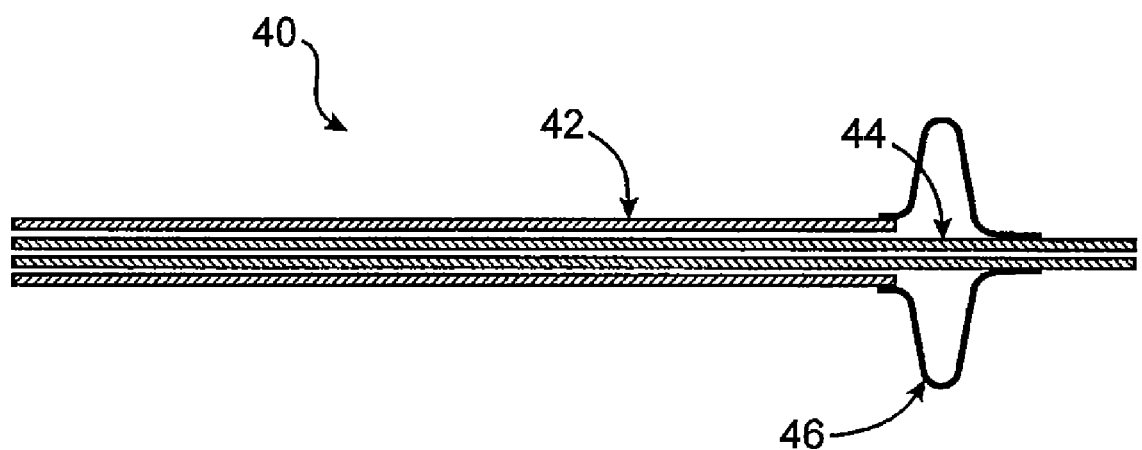

Referring now to FIGS. 4A and 4B, in another embodiment a catheter device 40 comprises an outer shaft 42, an inner shaft 44, and an anchoring member 46 coupled with both outer shaft 42 and inner shaft 44. Shafts 42, 44 are axially slidable relative to one another, such that when inner shaft 44 is moved proximally relative to outer shaft 42, anchoring member 46 buckles outward to perform its anchoring function, as shown in FIG. 4B. In this embodiment, inner shaft 44 acts as an injection lumen and also possibly as a guidewire lumen, and no inflation lumen is needed. In one embodiment, anchoring member 46 may be constructed as a cylinder with slots or other shapes cut out of it to form column-like buckling structures. Components of this embodiment may be made of the same or different materials as just described.

Figure 5A:
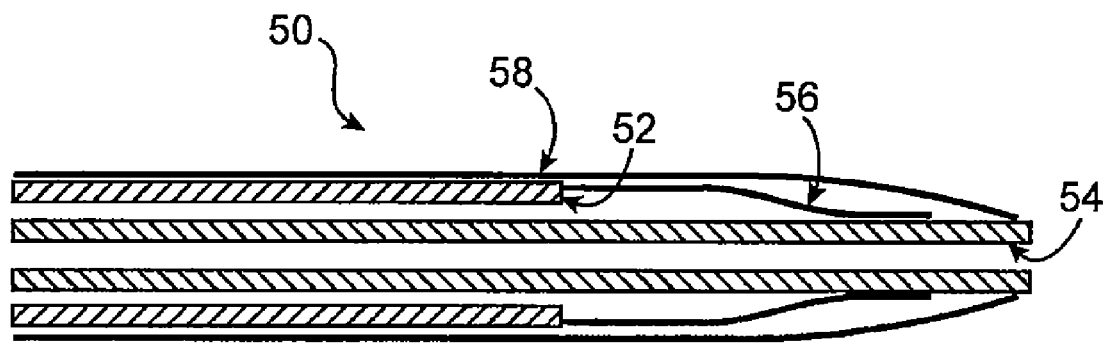
FIGS. 5A and 5B are cross-sectional views of a distal end of an alternative catheter device with an anchoring member in an undeployed and deployed state, respectively, according to another embodiment of the present invention.
Figure 5B:
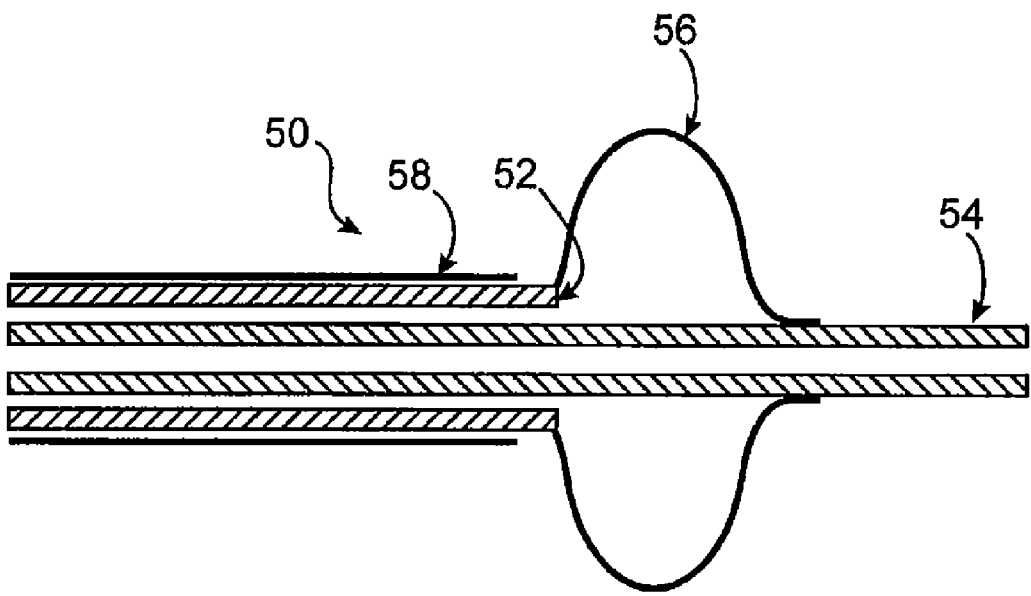

An alternative embodiment of a catheter device 50 is shown in FIGS. 5A and 5B. Here, catheter device 50 includes an outer shaft 52, an inner shaft 54, an anchoring member 56 coupled to outer shaft 52 and inner shaft 54, and a sheath 58 slidably disposed over outer shaft 52. When sheath 58 is disposed over anchoring member 56, as in FIG. 5A, anchoring member 56 remains in an undeployed state suitable for delivery into the disc. When sheath 58 is retracted and/or outer shaft 52 is advanced, as in FIG. 5B, anchoring member 56 may be deployed. In some embodiments, anchoring member 56 may be deployed via buckling or via inflation, as described above. In other embodiments, anchoring member 56 may self-expand, for example if it is comprised of shape-memory or spring-loaded materials that expand when released from sheath 58.

Figure 6A:
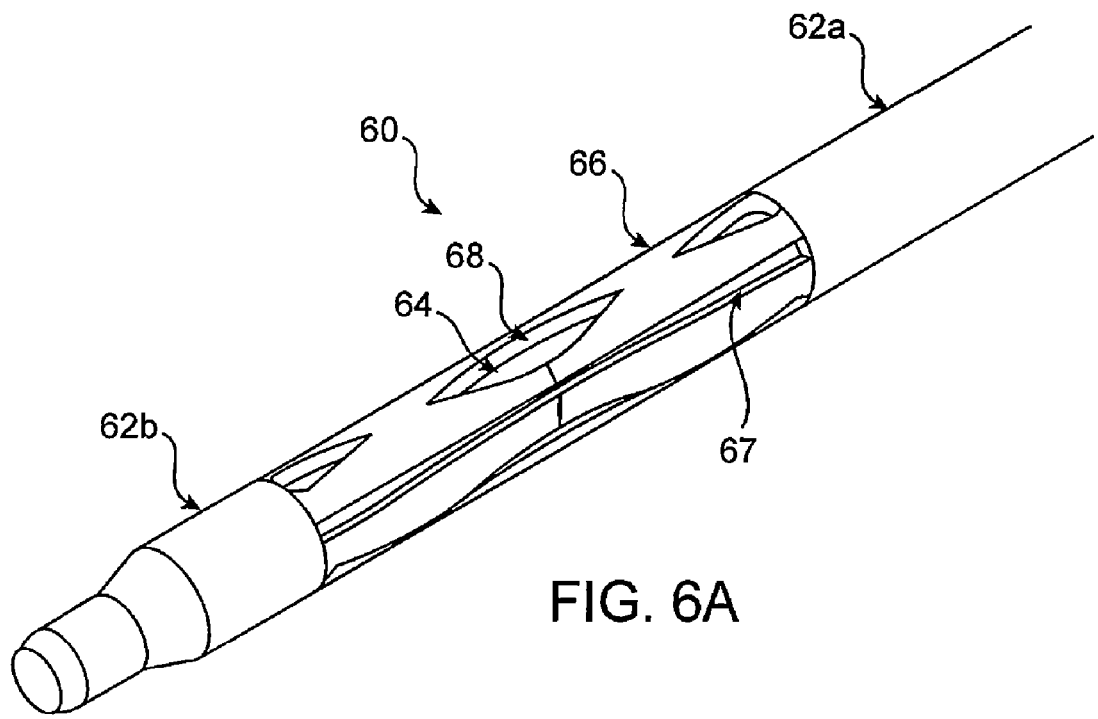
FIGS. 6A and 6B are cross-sectional views of a distal end of an alternative catheter device with an anchoring member in an undeployed and deployed state, respectively, according to another embodiment of the present invention.
Figure 6B:
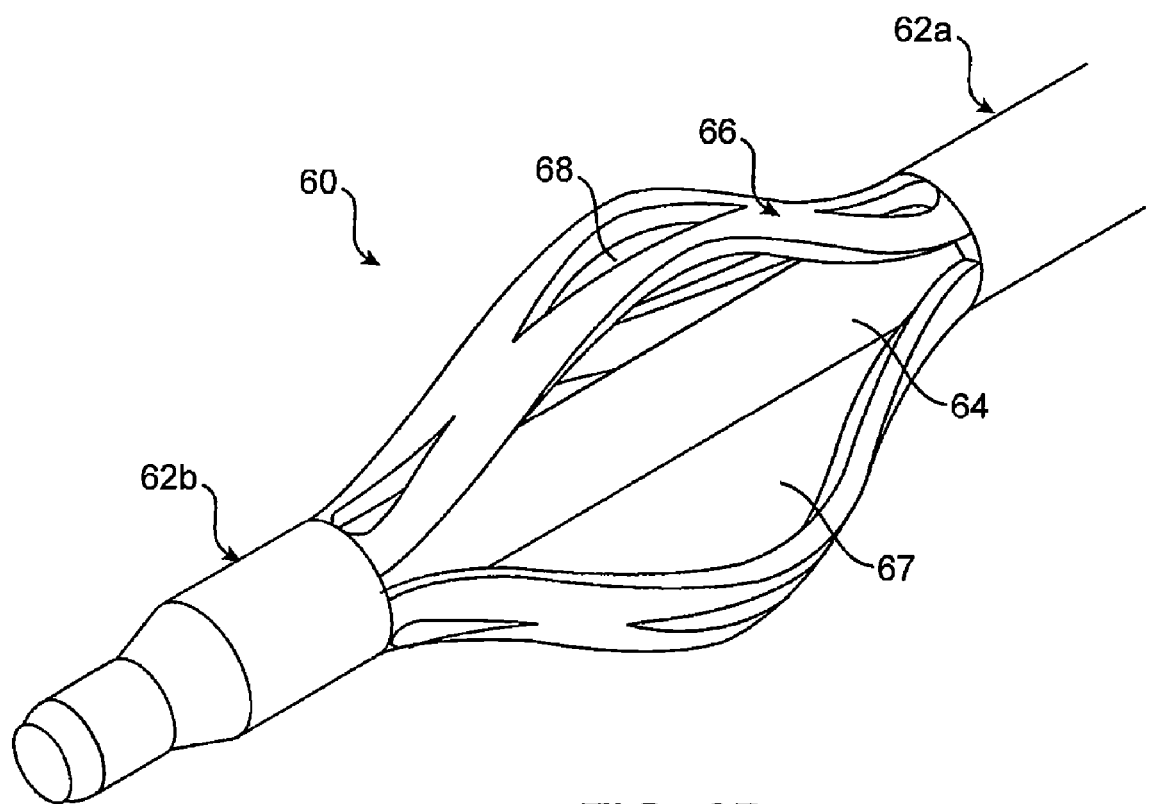

Referring now to FIGS. 6A and 6B, in another embodiment a catheter device 60 includes an outer shaft 62 having an expandable anchoring portion 66 and an inner shaft 64. Expandable anchoring portion 66 generally comprises a buckling portion of outer shaft 62 and may include multiple features such as small cut-outs 68 and larger openings 67. When a proximal portion of outer shaft 62a is moved toward a distal portion of outer shaft 62b, anchoring member 66 buckles, due to features 67, 68, thus providing the anchoring function.

Figure 7A:
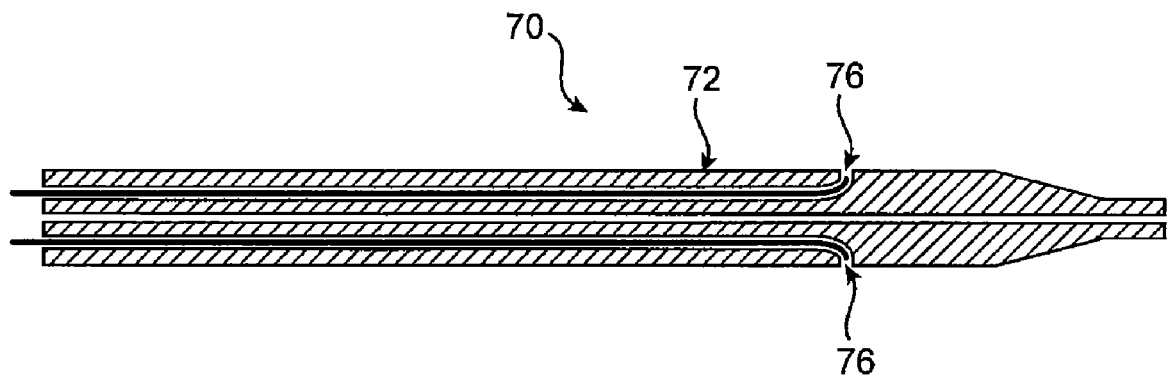
FIGS. 7A and 7B are perspective views of a distal end of an alternative catheter device with an anchoring member in an undeployed and deployed state, respectively, according to another embodiment of the present invention.
Figure 7B:
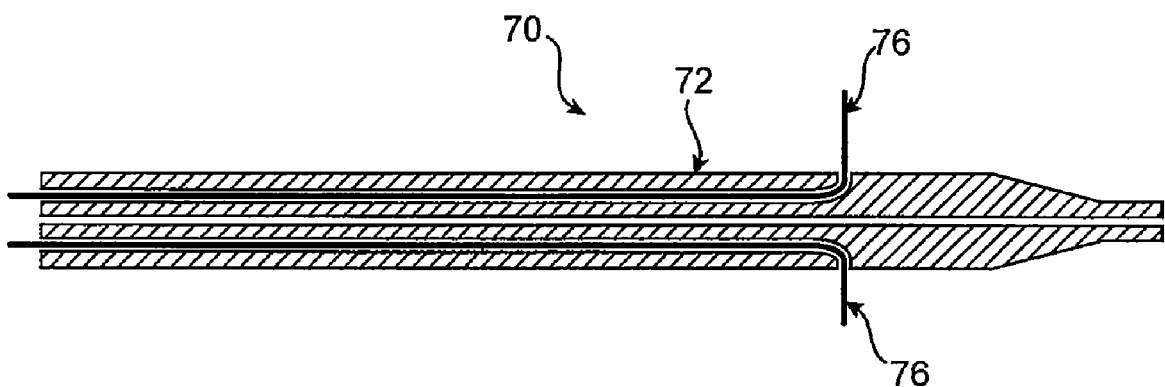

With reference now to FIGS. 7A and 7B, another embodiment of a catheter device 70 is illustrated having a catheter shaft 72 and retractable tine anchors 76. Tine anchors 76 may be deployed from a retracted state, as in FIG. 7A, to a deployed state, as in FIG. 7B. Tine anchors 76 may be pre-bent so that they readily take on a pre-determined shape when deployed out of catheter body 72, and anchors 76 may be made of metal, such as stainless steel or shape-memory metal such as Nitinol, polymers, or any other suitable material. In various embodiments, tine anchors 76 may be deployed either by pushing them out of their housing lumens or by releasing them from constraint to allow them to self-deploy.

Figure 8:
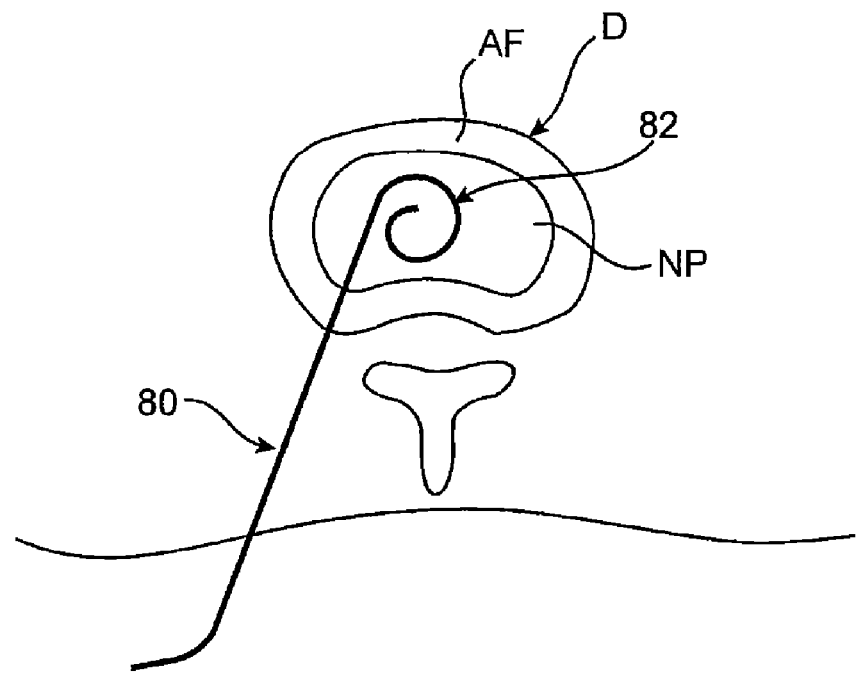
FIG. 8 illustrates a catheter device having a deforming, anchoring distal portion, according to one embodiment of the present invention.
Figure 9:
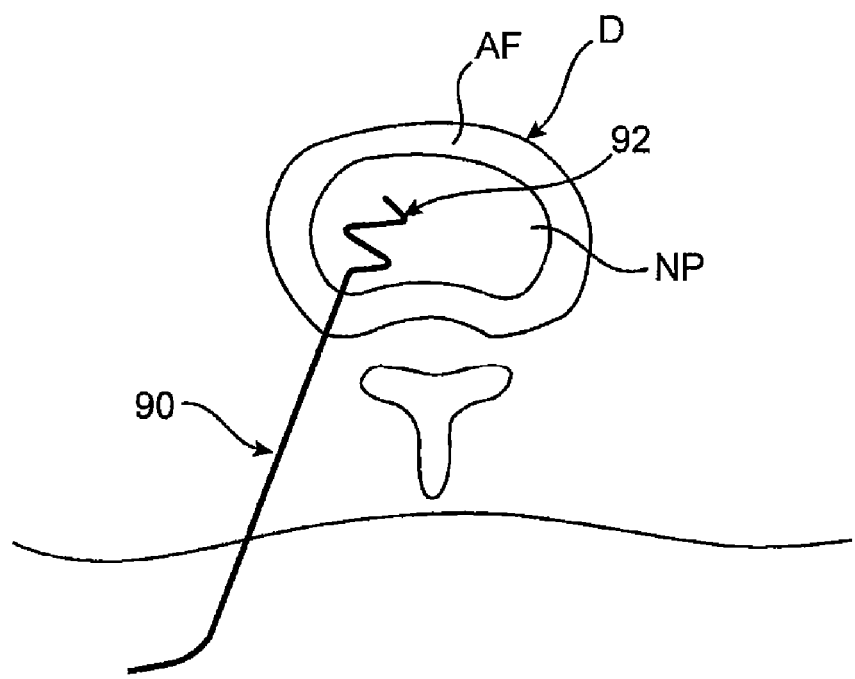
FIG. 9 illustrates a catheter device having a deforming, anchoring distal portion, according to another embodiment of the present invention.

In other embodiments, and with reference now to FIGS. 8 and 9, a distal portion of a catheter device may deform to anchor the distal portion in the disc D. In one embodiment, as in FIG. 8, a catheter device 80 may have a distal portion 82 that deforms to a spiral configuration. In another embodiment, as in FIG. 9, a catheter device may have a distal portion 86 that deforms to a zig-zag configuration. Any other suitable shape for a distal portion may be used in various embodiments. Deformation of a distal portion may be achieved by any suitable means, such as by using a shape-memory or spring-loaded material, by using a pull cord, tendon, stylet or other actuator to deform the distal portion or the like.

Figure 10A:
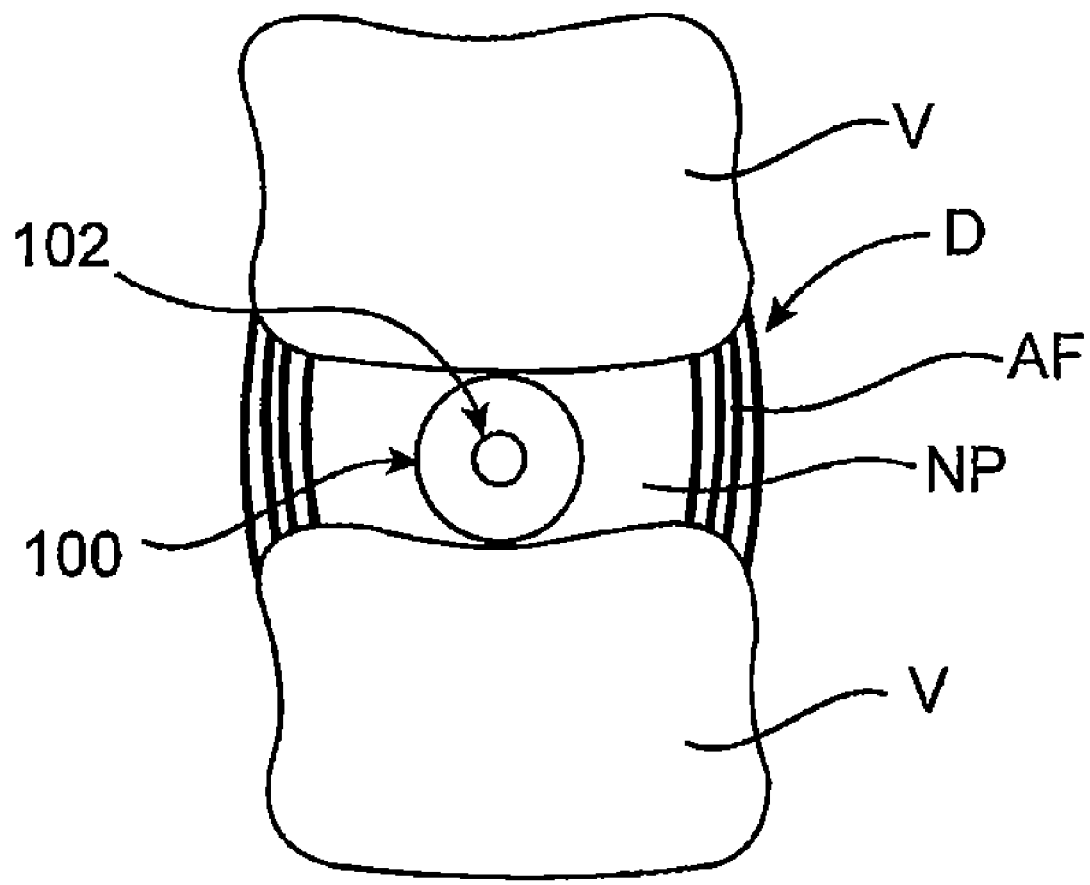
FIG. 10A illustrates a longitudinal cross-section of a spinal column with a catheter device with a radially symmetric anchor, according to one embodiment of the present invention.
Figure 10B:
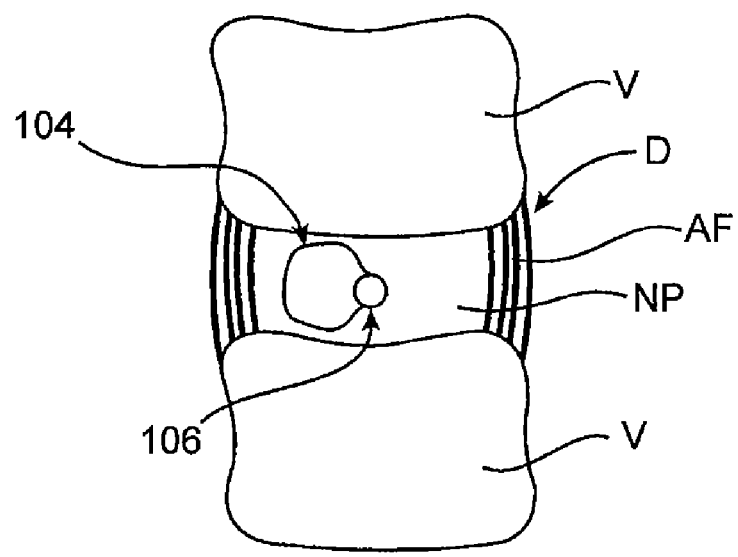
FIG. 10B illustrates a longitudinal cross-section of a spinal column with a catheter device with a radially asymmetric anchor, according to another embodiment of the present invention.
Figure 10C:
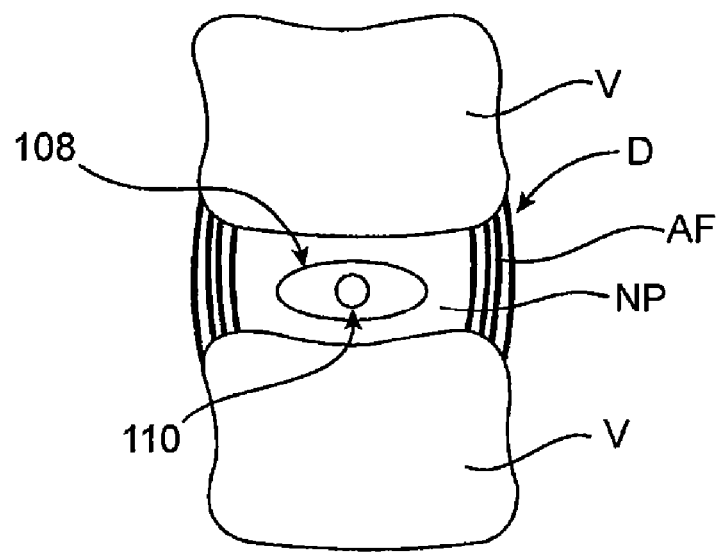
FIG. 10C illustrates a longitudinal cross-section of a spinal column with a catheter device with an elliptical shaped anchor, according to another embodiment of the present invention.
Figure 10D:
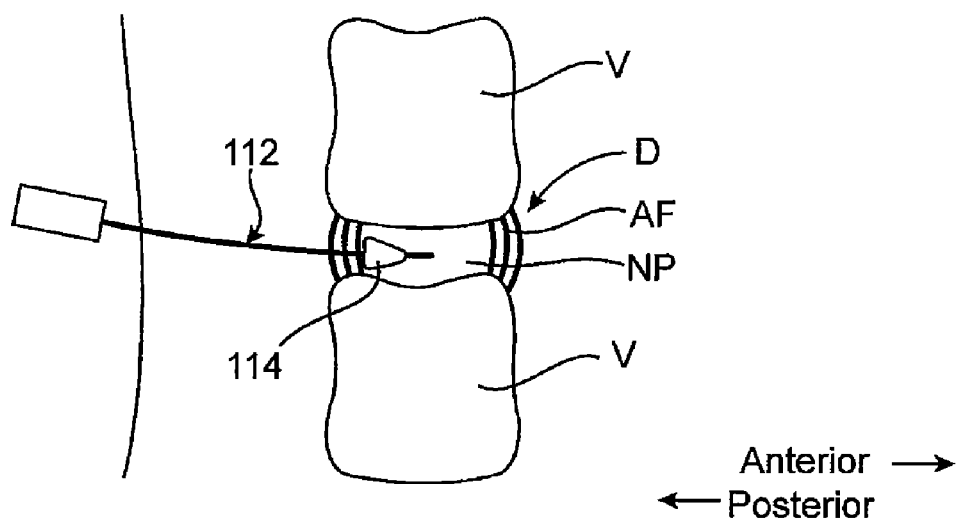
FIG. 10D illustrates a longitudinal cross-section of a spinal column with a catheter device with a non-spherically shaped anchor, according to another embodiment of the present invention.

FIGS. 10A-10D illustrate that an anchoring member of a catheter device may have any suitable shape, size, configuration, orientation to the catheter shaft or the like, in various embodiments. In the embodiment shown in FIG. 10A, for example, an anchoring member 100 of a catheter device is shown in cross-section within a disc D between two vertebrae V. In this embodiment, anchoring member 100 has a circular cross-sectional shape and is disposed concentrically over a catheter shaft 102 of the catheter device. In the embodiment shown in FIG. 10B, an anchoring member 104 is asymmetrically attached to a catheter shaft 106 and has a non-circular, asymmetric shape. In the embodiment shown in FIG. 10C, an anchoring member 108 is concentrically disposed over a catheter shaft 110 and has an elliptical cross-sectional shape. FIG. 10D shows a longitudinal view of a catheter device 112 having an approximately conical-shaped anchoring member 114. This embodiment demonstrates that anchoring member 114 may have not only various cross-sectional shapes but also various longitudinal shapes in various embodiments.

Figure 11:
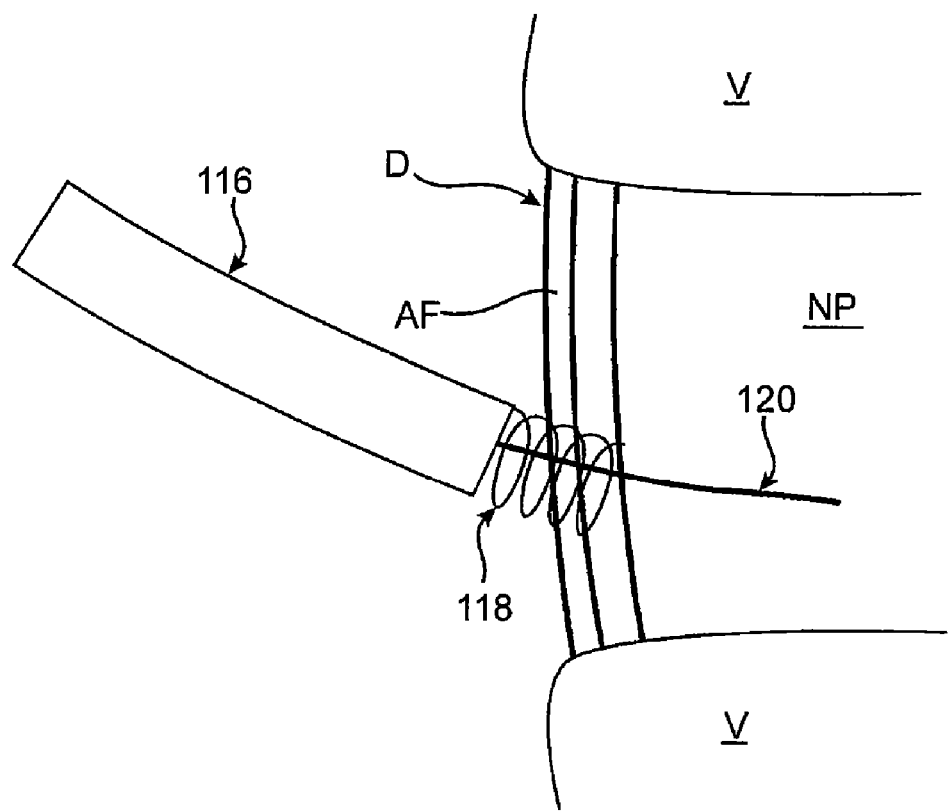
FIG. 11 illustrates a spiral anchor for attaching to the annulus fibrosis of an intervertebral disc, according to one embodiment of the present invention.

Referring now to FIG. 11, yet another embodiment of a catheter device 116 advanced over a guidewire 120 includes an anchoring member 118 that attaches to annulus fibrosis AF of a disc to maintain the distal portion of device 116 in the disc D. Here, anchoring member 118 comprises a spiral needle that may be screwed, twisted or otherwise driven into the annulus fibrosis AF.

Figure 12:
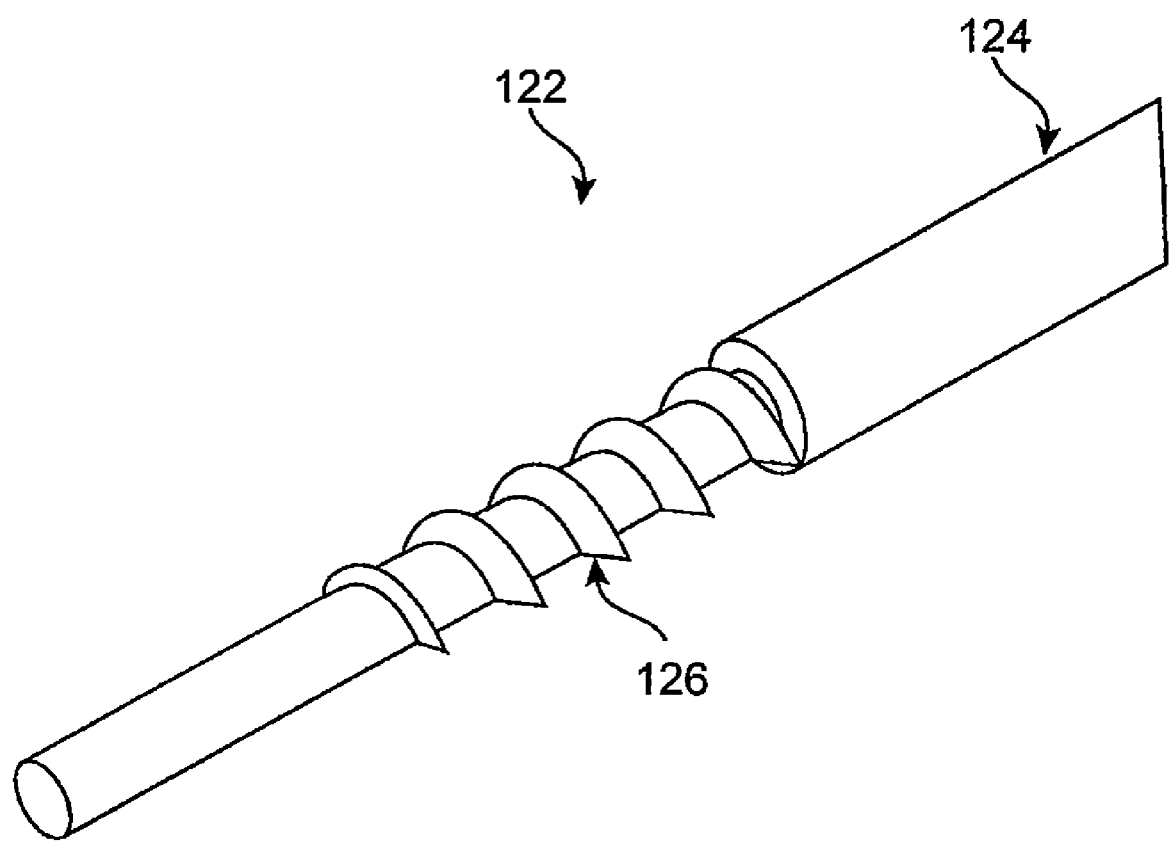
FIG. 12 illustrates a distal end of a catheter device having a threaded portion for attaching to an annulus fibrosis of an intervertebral disc, according to one embodiment of the present invention.

FIG. 12 shows another embodiment of a catheter device 122, in this case comprising a catheter shaft having threads 126 for anchoring in an annulus fibrosis. In various embodiments, any other suitable means for anchoring into the annulus fibrosis may be used, such as hooks, anchors, barbs, T-tags or the like.

Figure 13:
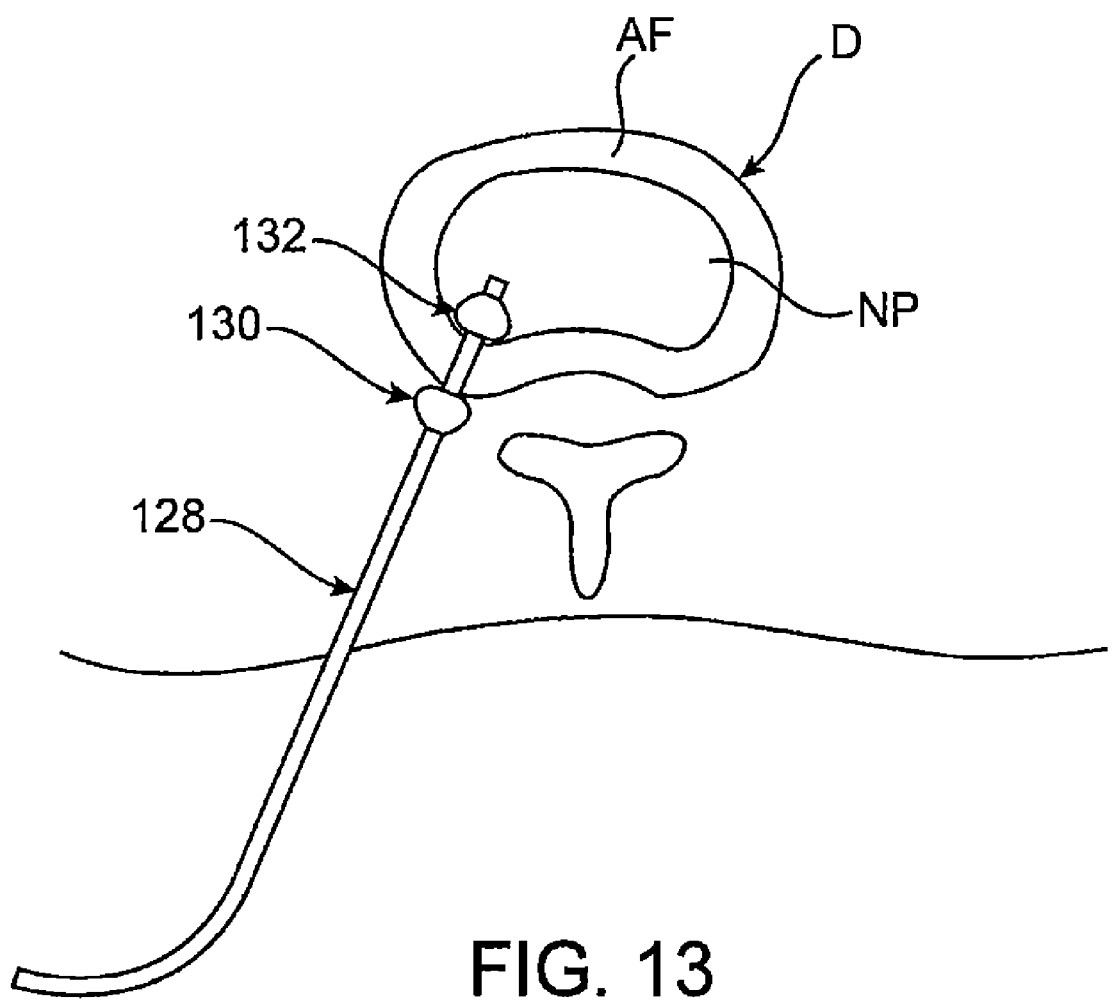
FIG. 13 illustrates a catheter device having two anchoring members for anchoring inside and outside an annulus fibrosis of an intervertebral disc, according to one embodiment of the present invention.

With reference now to FIG. 13, in another embodiment a catheter device 128 includes two an outer anchoring member 130 for anchoring outside the annulus fibrosis AF and an inner anchoring member 132 for anchoring inside the disc D, typically in the nucleus pulposus NP. As shown here, anchoring members 130, 132 may comprise expandable members, such as inflatable balloons. In other embodiments, alternative anchoring members may be used, more than two anchoring members may be used and/or the like. Using two anchoring members 130, 132 may further ensure that a distal portion of catheter device 128 remains in position within the disc.

Figure 14:
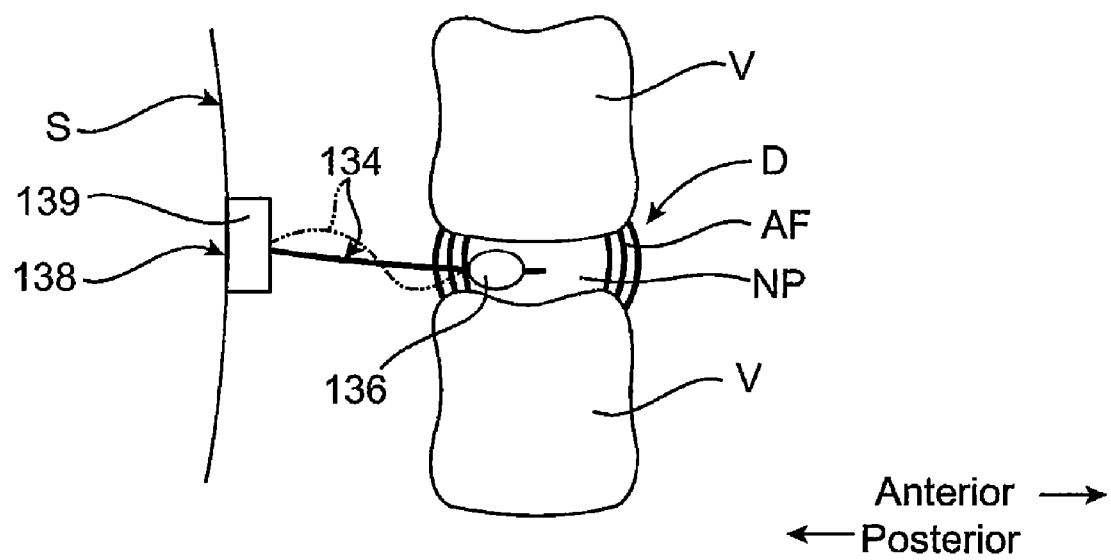
FIG. 14 illustrates a catheter device coupled with an implanted device for facilitating delivery of substances to the intervertebral disc, according to one embodiment of the present invention.

As discussed above, and referring now to FIG. 14, in some embodiments a catheter device 134 having an anchoring member 136 may be used for treating discogenic pain. In some embodiments, catheter device 134 may be coupled with an implantable device 138 for providing treatment, implantable device 138 being positioned under a patient's skin S or in any other suitable location in the patient's body. Implantable device 138 may comprise, for example, an implantable pump with or without a drug reservoir, an implantable drug infusion/injection port, transcutaneous electrical nerve stimulation (TENS) device or any other suitable device in various embodiments. Substances introduced into the disc DS via catheter device 134 and implantable device 138 may include any of the substances listed above, such as an anesthetic or analgesic to relieve pain. Implantable device 138 may be left in the patient for any suitable length of time to provide treatment.

In one embodiment, implantable device 138 may comprise an implantable pump 139. In some embodiments the pump may be programmed to deliver drug from an attached reservoir into the nucleus pulposus at a constant rate, at programmed intervals, upon triggering by the patient or physician through the use of an external device capable of communicating with the pump, such as but not limited to magnetic reed switches, electromagnetic wave communication devices such as visible light, radio-wave, microwave, or short-wave, or wireless communication protocols such as Bluetooth. In some embodiments, the patient may control pump-mediated drug delivery by physically manipulating switches, toggles, or other similar devices coupled with the pump. Optionally, the implantable pump may be configured to store data related to the usage pattern of the drug by the patient. This information could be downloaded for review through wireless communication with an external device such as those listed above. In embodiments having a drug reservoir, the implantable device may also include an injection port to allow the reservoir to be refilled transcutaneously.

The distance between the disc D and the surface of the skin can change as the patient moves. To prevent the distal end of catheter device 134 and anchoring member 136 from pulling out of the nucleus, a mechanism for providing strain relief in the attachment between catheter device 134 and implantable device 138 may be provided. In one embodiment, for example, catheter device 134 may extend between implantable device 138 and the disc D in a circular, spiral, curved, serpentine, or otherwise nonlinear path, thus providing an amount of slack (as shown in broken line) in catheter device to allow for movement between the disc D and the implantable device 138 with patient movement.

Implantable catheter devices, such as catheter device 134, will be provided with anchoring members 136, which typically may be inflatable balloons or other structures. Preferably, the catheter devices 134 will have an integral balloon inflation lumen, or will be provided with separate balloon inflation tubes to permit inflation of the balloon anchor 136 after proper positioning of the catheter. Rather than using a stopcock or other valve structure for providing balloon inflation, the catheter devices 134 may be provided with self-sealing septum structures at an end of the inflation lumen. Optionally, the catheter devices 134 could also include substance delivery lumens which also terminate at a proximal end in a self-sealing septum to allow for drug and substance delivery after the device has been implanted. Suitable septum materials include silicone, rubber, latex rubber, isoprene rubber, polyisoprene rubber, and numerous other known materials.

Alternatively, a balloon inflation lumen on the catheter device 134 or separate balloon inflation tube could be sealed using a suture, clip, filament loop, or any of a variety of other external closure elements. Such clips or crimps could be formed from a spring-like material, such that they can be pre-shaped to collapse the inflating lumen. Alternatively, the clips or crimps could be deformable so that they could be tightened over the balloon inflation lumen to effect closure. In both cases, multiple closure members could be placed at different points along the balloon inflation lumen in order to enhance the seal. Moreover, the closure elements could be removable to permit deflation and reinflation of the balloon, should it be desired during or after implantation. The closure elements could also be removed to permit deflation of the balloon for explantation of the catheter.

As a further alternative, the balloon inflation lumen could be sealed using heat, adhesives, or ultrasonic energy, resulting in melting or fusing of the lumen. Heat can come from a variety of sources, including electrical resistance heaters, electrical inductive heaters, or the like.

Figure 15A:
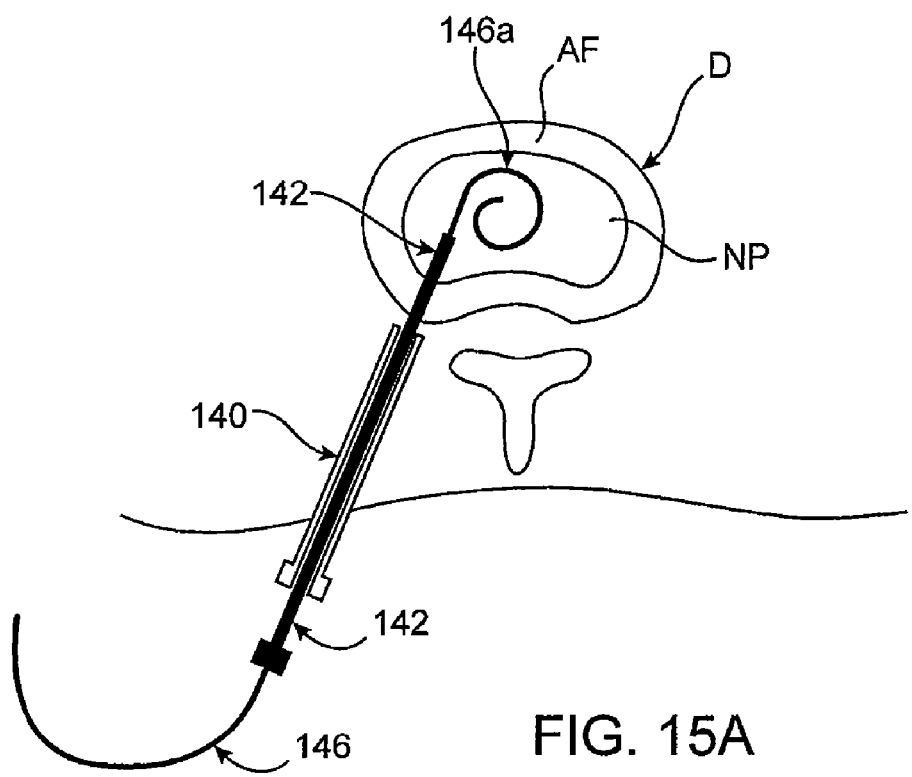
FIG. 15A illustrates a catheter device passed over a guidewire having a spiral-shaped distal end, according to one embodiment of the present invention.

To facilitate delivery of a distal portion of a catheter device into a disc D, and with reference now to FIG. 15A, some systems include a shaped guidewire 146 configured to maintain a distal portion of guidewire 146 within the disc during delivery of the catheter device. As shown in FIG. 15A, guidewire 146 is delivered through an injection needle 142, which has been delivered through an introducer device 140. When a distal portion of guidewire 146a is advanced out of the distal end of injection needle 142, it assumes a shape, in this case a spiral shape, which secures distal portion 146a in the disc. Guidewire 146 may be formed of any suitable material to provide for such a shape change, such as but not limited to shape-memory materials such as Nitinol, spring stainless steel or the like. In some embodiments, a distal tip of the guidewire includes one or more radiopaque markers, coils or the like, or is made of one or more radiopaque materials.

Figure 15B:
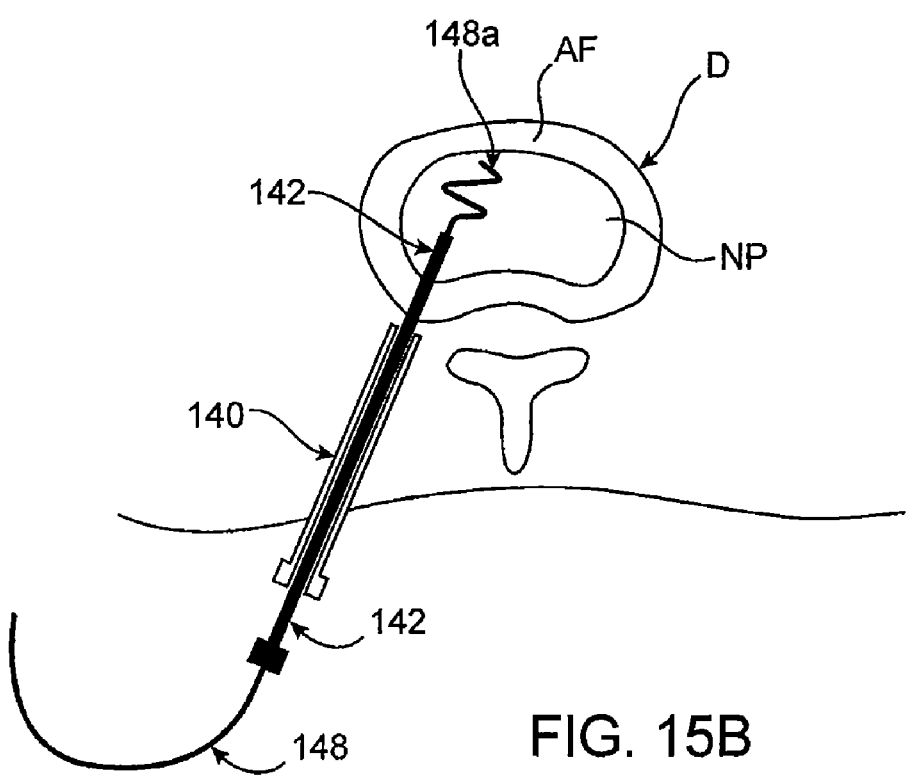
FIG. 15B illustrates a catheter device passed over a guidewire having a zigzag-shaped distal end, according to another embodiment of the present invention.

As shown in FIG. 15B, in another embodiment a guidewire 148 has a distal portion 148a that assumes a zig-zag shape upon being advanced beyond the distal end of injection needle. In various embodiments, guidewires may have distal portions with any suitable shapes for anchoring in the disc D.

Figure 16A:
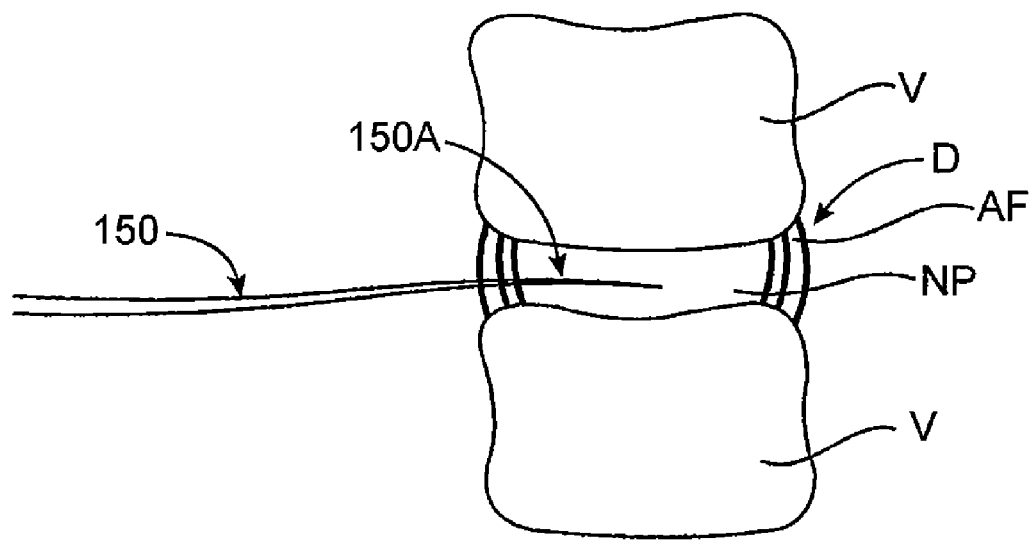
FIGS. 16A and 16B illustrate a double-wire guidewire in undeployed and deployed states, respectively, according to one embodiment of the present invention.
Figure 16B:
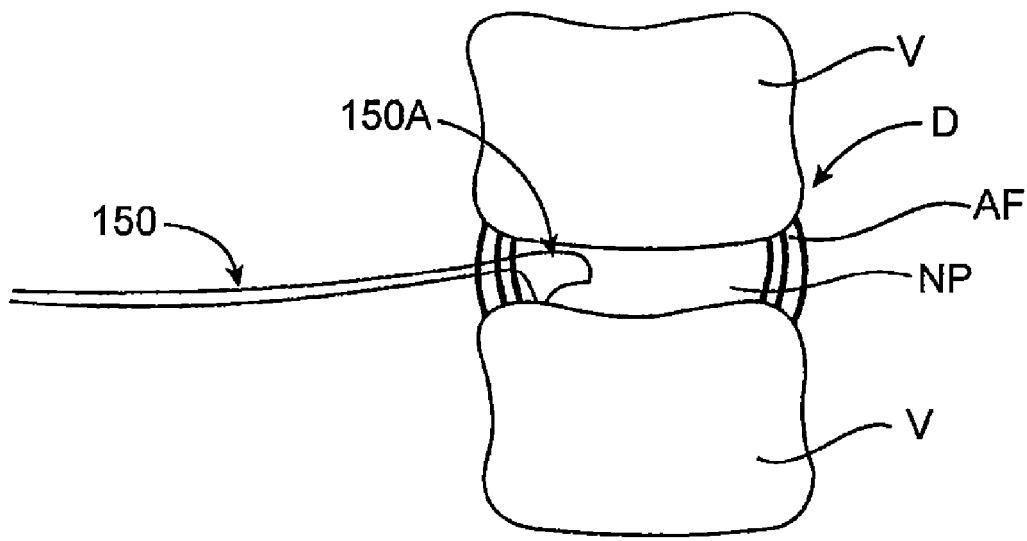

Referring now to FIGS. 16A and 16B, in one embodiment a guidewire 150 has a double-wire configuration for enhancing its ability to maintain its position within a disc D. Double-wire guidewire 150 includes two wires joined at their distal ends, the attachment being achieved by welding, soldering, bonding, gluing, folding a single wire, or any other suitable technique. As shown in FIG. 16A, a distal end of guidewire 150a may be delivered into the disc D in a relatively straight, undeployed configuration. Double-wire guidewire 150 is then deployed, as shown in FIG. 16B, by differentially pushing or pulling on one of the wires of the double wire guidewire causing distal portion 150a to deform. In its deployed state, double-wire guidewire 150 is less likely to dislodge or pull out of the disc D than a single-wire guidewire.

Figure 14A:
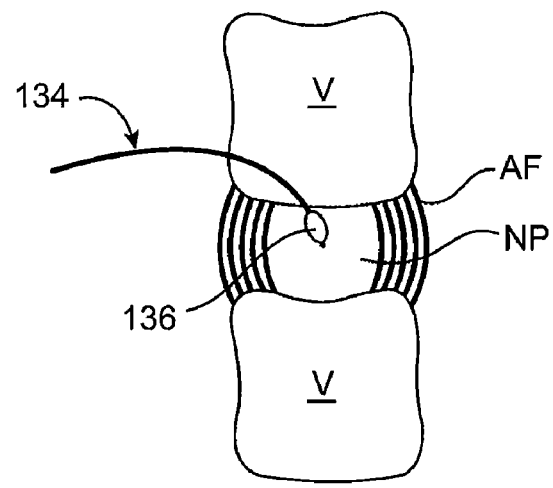
FIGS. 14A and 14B illustrate introduction of a treatment or other access catheter into a disc space using a transosseous approach.
Figure 14B:
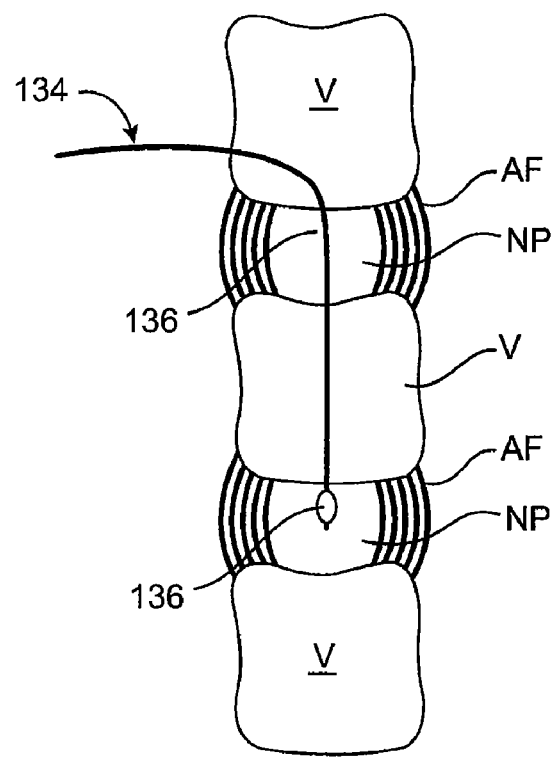

As described thus far, the disc space has been accessed using a transannular approach. As illustrated in FIGS. 14A and 14B, however, in some cases it may be preferable to approach the nucleus pulposus NP through the adjacent vertebral body V in a transosseous approach, i.e., across the bone. Use of a transosseous approach avoids the necessity of performing an annulotomy, thus avoiding puncturing and potentially damaging the annulus fibrosis AF. In the transosseous approach, the catheter 134 passes through the vertebral body V and into the disc space. As shown in FIG. 14A, the catheter 134 may pass through a single vertebral body into the adjacent disc space. In some cases, however, it may be desirable to pass the catheter 134 through multiple disc spaces, as shown in FIG. 14B, deploying the anchoring member 136 in the distal-most disc space, or alternatively in one of the vertebral bodies. Such an approach is advantageous since it permits treatment of multiple disc spaces simultaneously. The disc space or spaces could be accessed from the superior or inferior vertebral body. The transosseous approach could be performed by drilling or chiseling an access path through the vertebral body using a twist drill bit, a abrasive burr, sharp chisel, or other tools known in the art of surgery. The tool utilized to make the access path in the bone can be introduced alone or through the introducer needle. In some cases it may be necessary to pre-bend the introducer needle or tool to achieve the correct angle for the access hole in the vertebral body.

Figure 17A:
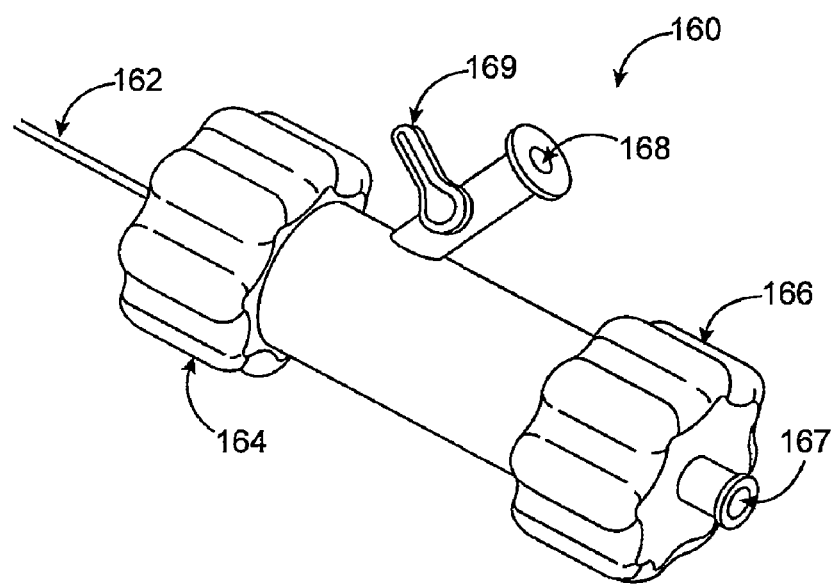
FIGS. 17A and 17B are perspective and cross-sectional views, respectively, of a proximal adapter for use with a catheter device, according to one embodiment of the present invention.
Figure 17B:
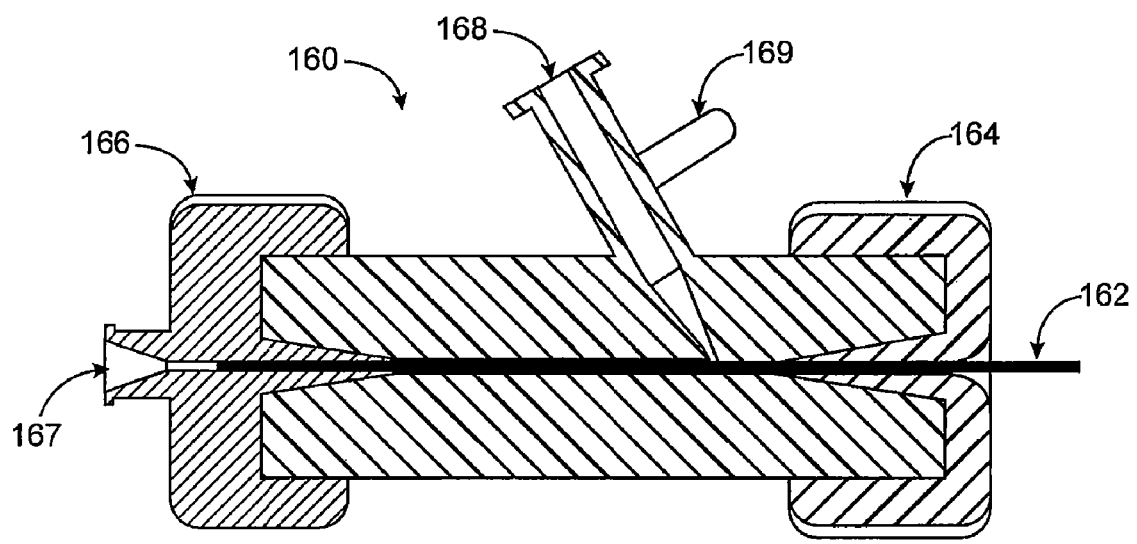

With reference to FIGS. 17A and 17B, one embodiment includes one or more adapters 160 for removably coupling with one or more proximal ends of a catheter device 162. Adapter 160 is typically coupled with catheter device 162 after the distal end of catheter device 162 is in place within the disc and after the introducer device, stylet or the like has been removed, although in alternative embodiments adapter 160 may be coupled with catheter device 162 at any other suitable time. Adapter 160 may comprise or resemble a Touhy Bourst adapter, compression fitting, instant tube fitting, or other similar adapter or connector. In one embodiment, adapter includes a distal sealed connector 164, a proximal sealed connector 166 having an injection port 167, an anchoring member inflation port 168, and a stopcock 169 for controlling fluid flow through inflation port 168. Injection port 167 is in fluid communication with a lumen of catheter device 162 and may be used for injection of substance(s) into the disc and/or for passage of a guidewire. Injection port 167 and inflation port 168 may include leur fittings, press fits, barbs or any other suitable tube connection methods. Proximal sealed connector 166 and distal sealed connector 164 may be activated by rotating the sealed connectors on threads, automatic press activation, spring actuation or any other suitable method.

In addition to implantable devices and proximal adapters, a catheter device in some embodiments may be coupled with one or more automated injection devices. Such injection devices may facilitate testing of one disc or multiple discs over an extended period of time, with only periodic supervision by a physician, nurse or other clinician. For example, the patient could remain in clinic or hospital room while a series of substances are introduced into a disc, while the patient assumes different positions to test the pain response, while substances are injected into multiple discs through multiple catheter devices and/or the like. Such an automated system may facilitate and enhance diagnosis of discogenic pain by allowing for more extensive testing. In some embodiments, such a system may also include a device for recording patient pain responses, such as an instrument that allows a patient to record pain felt before and after an injection on a scale from 1 to 10 and/or to relate the pain felt to the patient's usual back pain.

Although the foregoing is a complete and accurate description of the invention, a number of changes, additions, variations and the like may be made to various embodiments without departing from the scope of the invention. Therefore, the description is provided primarily for exemplary purposes and should not be interpreted to limit the scope of the invention as set forth in the claims.

What is claimed is:

1. A method comprising:
   inserting a catheter into an intervertebral disc in a patient's body, the catheter having an expandable member;
   expanding the expandable member of the catheter within the intervertebral disc to anchor the catheter within the intervertebral disc;
   introducing a substance through the catheter into the intervertebral disc in the patient's body automatically via an automated injection device; and
   treating the intervertebral disc with the introduced substance, wherein the substance is an anesthetic.

2. The method according to claim 1, wherein the substance is introduced through the catheter while the catheter is anchored in the intervertebral disc.

3. The method according to claim 1, wherein the expandable member is configured to increase a cross-sectional diameter of the catheter at one or more locations on the catheter.

4. The method according to claim 1, further comprising:
instructing the patient to assume various back-pain-generating positions; and
recording one or more patient inputs describing back pain experienced by the patient.

5. The method according to claim 1, further comprising:
identifying the intervertebral disc as a source of the patient's pain.

6. The method according to claim 1, further comprising identifying the intervertebral disc as a possible source of the patient's pain before introducing the substance.

7. A method comprising:
inserting a catheter into an intervertebral disc of a patient's body, the catheter having an expandable member;
expanding the expandable member of the catheter within the intervertebral disc to anchor the catheter within the intervertebral disc;
introducing a substance into the intervertebral disc in the patient's body with an automated injection device;
treating the intervertebral disc with the introduced substance;
instructing the patient to assume various back-pain-generating positions; and
recording one or more patient inputs describing back pain experienced by the patient,
wherein the substance comprises an anesthetic.

8. The method according to claim 7, further comprising:
identifying the intervertebral disc as a possible source of the patient's pain before introducing the substance.

9. The method according to claim 7, wherein expanding the expandable member comprises increasing a cross-sectional diameter of the catheter at one or more locations on the catheter.

10. The method according to claim 7, wherein the substance is introduced through the catheter while the catheter is anchored in the intervertebral disc.

11. The method according to claim 7, further comprising:
identifying the intervertebral disc as a source of the patient's pain.

* * * * *